United States Patent [19]
Allington

[11] 4,099,921
[45] Jul. 11, 1978

[54] CHEMICAL ANALYZER

[75] Inventor: Robert William Allington, Lincoln, Nebr.

[73] Assignee: Instrumentation Specialties Company, Lincoln, Nebr.

[21] Appl. No.: 781,765

[22] Filed: Mar. 28, 1977

[51] Int. Cl.² .................... G01N 33/16; G01N 1/14
[52] U.S. Cl. ................................. 23/253 R; 23/259
[58] Field of Search ............... 23/230 R, 253 R, 259; 141/130

[56] References Cited

U.S. PATENT DOCUMENTS

| | | | |
|---|---|---|---|
| 3,533,744 | 10/1970 | Unger | 23/253 R |
| 3,802,782 | 4/1974 | Natelson | 23/253 R |
| 3,897,216 | 7/1975 | Jones | 23/259 |
| 3,917,455 | 11/1975 | Bak et al. | 23/259 X |
| 3,985,507 | 10/1976 | Litz et al. | 23/253 R |
| 3,985,508 | 12/1976 | Williams | 23/259 X |
| 4,039,287 | 8/1977 | Moran | 23/253 R |

*Primary Examiner*—R.E. Serwin
*Attorney, Agent, or Firm*—Vincent L. Carney

[57] ABSTRACT

To transfer fluids between receptacles at controlled times and temperatures for analysis of the fluids, the receptacles are carried by shuttles which are replaceable and movable within the chemical analyzer and have fluids deposited in them automatically at predetermined times and locations under the control of a program card as they move through temperature-controlled zones at speeds established to keep the receptacles in the temperature-controlled zones long enough to complete a reaction. Two of the shuttles are driven and pull or push the other shuttles in a circular path. In one embodiment, a second circle of shuttles or a reel carrying receptacles moves in the reverse direction from a first group of shuttles so that fluids may be transferred from one receptacle to another at predetermined points to provide greater flexibility in the analyzing apparatus.

18 Claims, 20 Drawing Figures

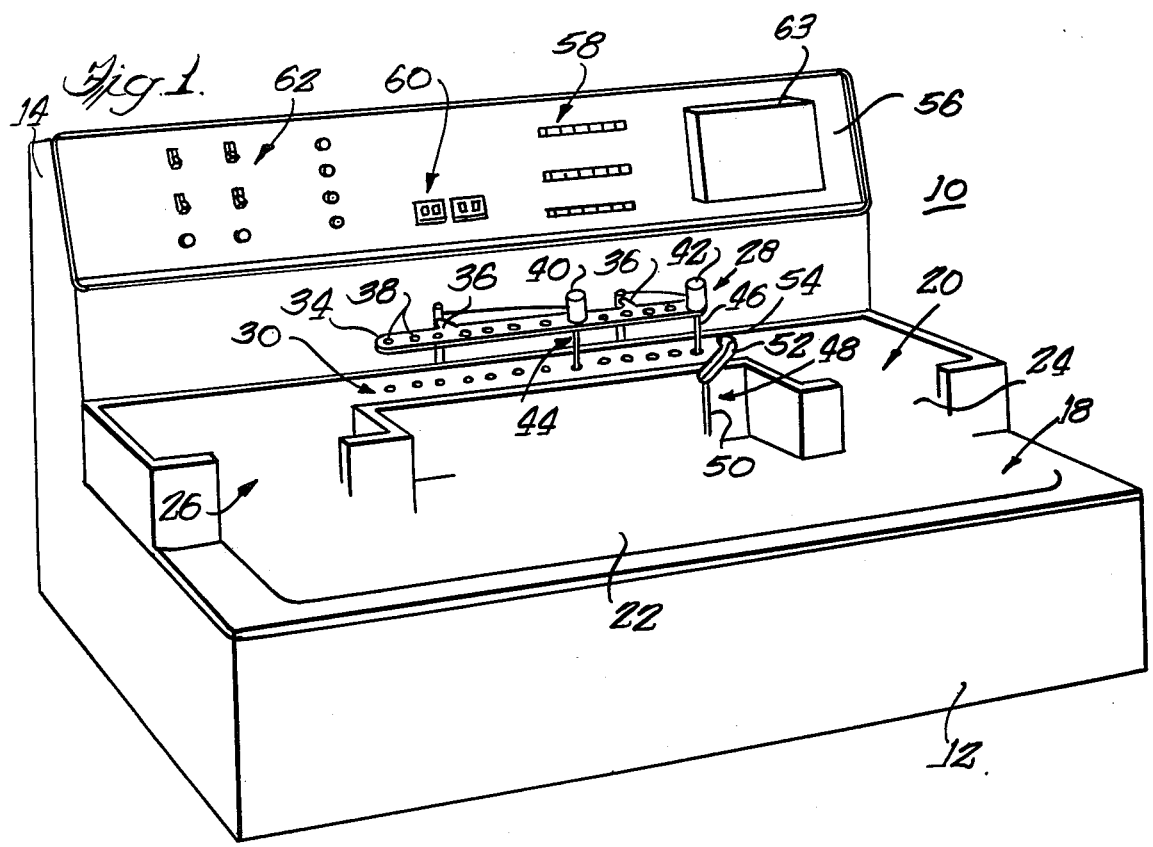
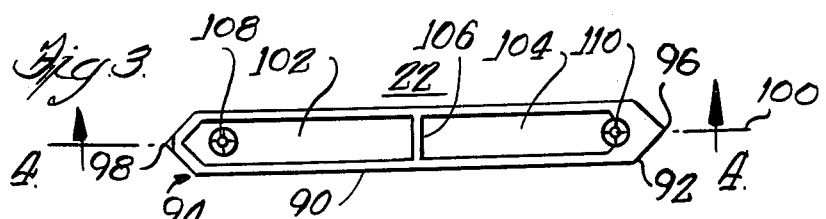
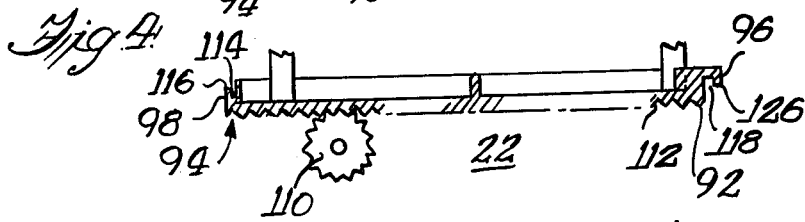
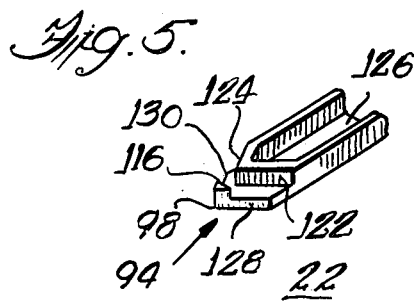
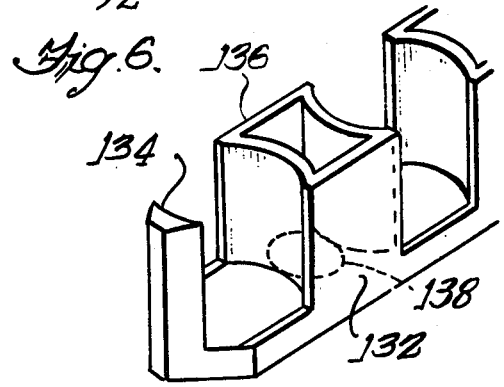

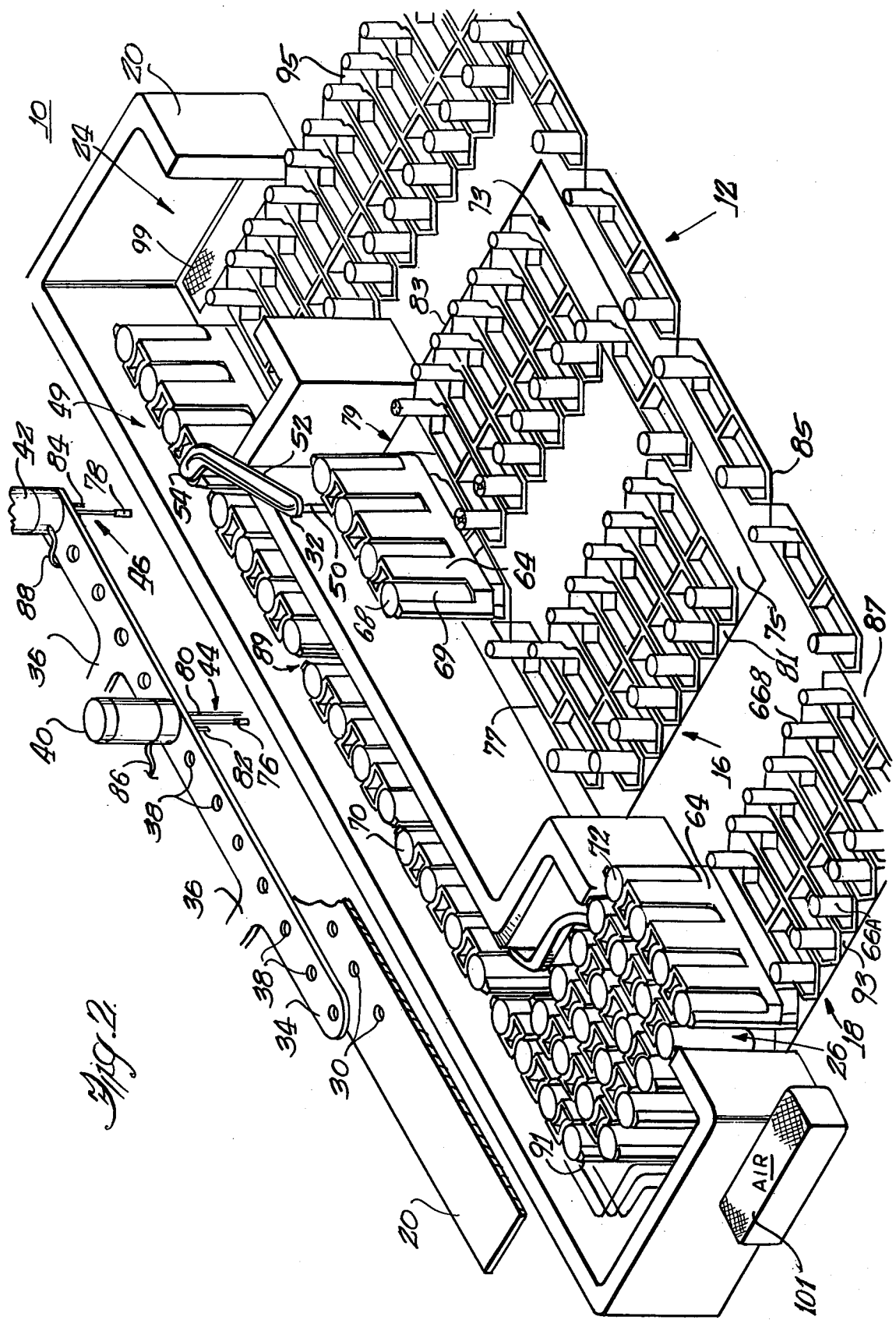

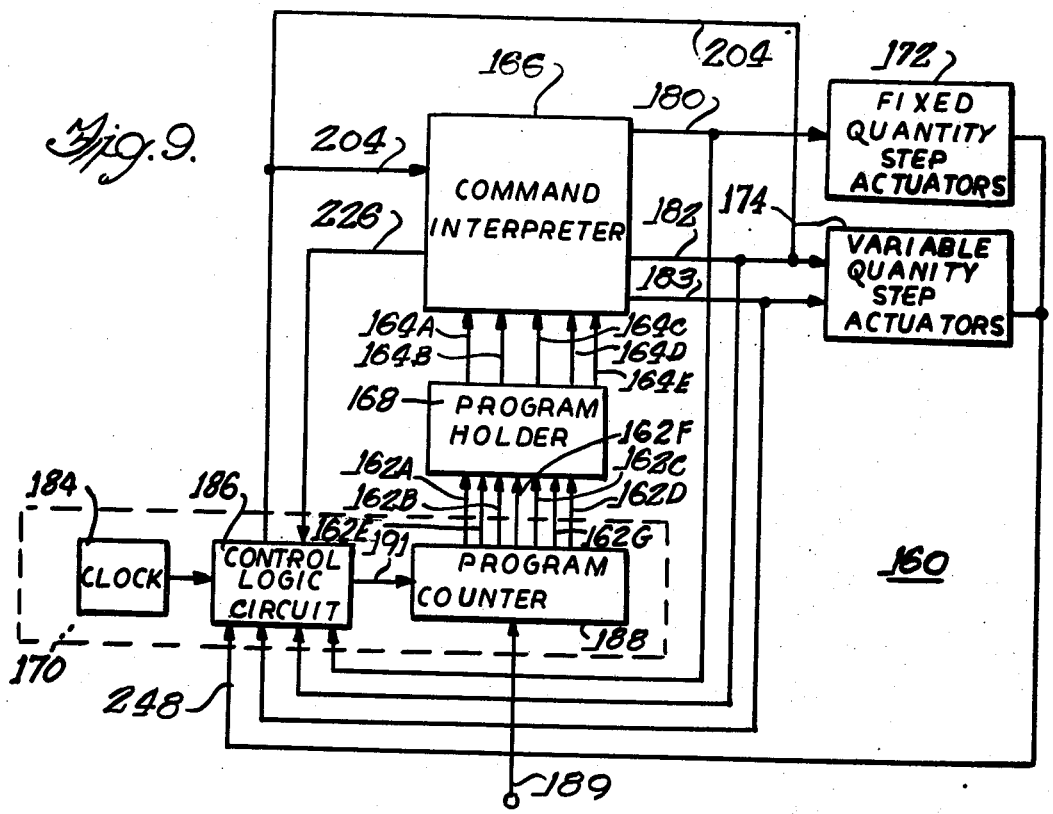

CHEMICAL ANALYZER

This invention relates to automatic chemical analyzers.

In one class of chemical analyzer, receptacles containing fluids are moved at a predetermined speed between stations a predetermined distance apart, which stations deposit other fluids into the receptacles, withdraw fluids from the receptacles, transfer fluids from one receptacle to another or analyze the fluids in the receptacles. The distance between stations and the temperature are selected to correspond to the desired time of reaction of the fluids before the next operation is performed.

In a prior art chemical analyzer of this class, the receptacles are held in fixed compartments which move with a rotating reel or along a conveyor, so that the single-drive mechanism continuously drives a single member containing a large number of receptacles.

This type of prior art apparatus has several disadvantages, such as: (1) the drive mechanism is complicated; and (2) it is difficult to remove and exchange the receptacles.

Apparatuses are known in which a plurality of receptacles are driven and which do not have the complicated structure of the above-mentioned prior art type of chemical analyzer. However, these apparatuses are not suitable for controlling the time of chemical reaction or for performing the operations necessary in a chemical analyzer.

Another prior art type of chemical analyzer incorporates programmed computer control of the operations. Examples are given by the following publications: Eggert et al, ANALYTICAL CHEMISTRY, 43, 6, 736-747 (1971); Cembrowski et al, COMPUTERS & CHEMISTRY, 1, 45-54 (1976); Toren et al, CLINICAL CHEMISTRY, 19, 10, 1114-1127 (1973) and Deming et al, ANALYTICAL CHEMISTRY, 43, 2, 192-200 (1971). These publications disclose a number of flexible programming methods based upon conventional computer control practice. However, chemical analyzers incorporating these controllers suffer the defect of having an inefficient sample handling system that decreases their throughput rate when long reaction times are required.

In still another prior art chemical analyzer of this class, a computer controls the motion of racks holding serum cups and reaction cups. The racks carry the cups between a first station which may dispense serum and a plurality of reagents into a reaction cup and a second station which picks up the sample from the reaction cups after an incubation time determined by the time it takes to move between stations. This time is controlled by the computer. This analyzer has the disadvantage that only up to five samples can be actively involved in processing at a time. Since processing cannot take place throughout the sample changer, its throughput rate is limited.

Accordingly, it is an object of the invention to provide a novel chemical analyzer.

It is a further object of the invention to provide a chemical analyzer which is simple in construction and inexpensive.

It is a still further object of the invention to provide a chemical analyzer with flexibility and ease of adapting to different operations.

It is a still further object of the invention to provide a chemical analyzer in which the receptacles are carried by shuttles that are freely substitutable for other shuttles within the chemical analyzer.

It is a still further object of the invention to provide a chemical analyzer in which a relatively small number of shuttles that carry receptacles for the chemicals are directly driven and these relatively few shuttles drive other shuttles to form a continuous line of motion of the receptacles within the analyzing apparatus.

It is a further object of the invention to provide a chemical analyzer in which shuttles containing chemicals are driven in two different closed paths in different directions with respect to each other, one closed path being within the other so that fluids may be transferred between receptacles containing a different number of reagents at a fixed station with the reagents being changeable in accordance with a fixed program.

In accordance with the above and further objects of the invention, a chemical analyzer includes a cabinet having a temperature control zone, a receptacle transport section and a plurality of fluid transfer stations. Within the fluid transport section, a plurality of shuttles are driven by a drive mechanism that engages the bottoms of relatively few shuttles, with the few shuttles driving the remainder of the shuttles in a closed path past the stations and through the temperature control zone. The rate of travel of the shuttles and the temperature of the temperature control zones are selected to correspond with a desired reaction time between the fluid transfer stations which deposit the fluids onto, remove fluid from or transfer fluids between receptacles in the shuttles. In one embodiment, one group of shuttles is moved in a first direction in a closed path forming an outer receptacle transport section and another group of shuttles or reel holding containers is moved in a second closed path within the first group forming an inner receptacle transport section. With this arrangement, a reagent in a receptacle in the inner receptacle transport path is transferred into a plurality of receptacles in the outer receptacle transport path, after which, the position of the receptacles in the inner transport path is changed and new reagent is introduced into receptacles in the outer transport path.

This chemical analyzer has several advantages, such as: (1) it is simple and inexpensive; (2) the shuttles may be easily removed and new ones inserted, thus permitting greater flexibility; and (3) flexibility in the type of analysis being performed is enhanced, in one embodiment, by the two groups of shuttles which are movable in opposite directions.

The above-noted and other features of the invention will be better understood from the following detailed description when considered with reference to the accompanying drawings in which:

FIG. 1 is a perspective view of a chemical analyzer in accordance with one embodiment of the invention;

FIG. 2 is a fragmentary perspective view of the chemical analyzer of FIG. 1, broken away to show inner and outer receptacle transport paths of the embodiment of FIG. 1;

FIG. 3 is a plan view of a shuttle used in an embodiment of the invention;

FIG. 4 is a fragmentary longitudinal, sectional view of the shuttle of FIG. 3;

FIG. 5 is a fragmentary perspective view of a portion of the shuttle of FIG. 3;

FIG. 6 is a fragmentary perspective view of a receptacle holder which cooperates with the shuttle of FIG. 3;

FIG. 9 is a block diagram of a programming system useful in an embodiment of the invention;

FIG. 10 is a logic diagram of a command interpreter which is a part of the programming system shown in FIG. 9;

Figure 7:
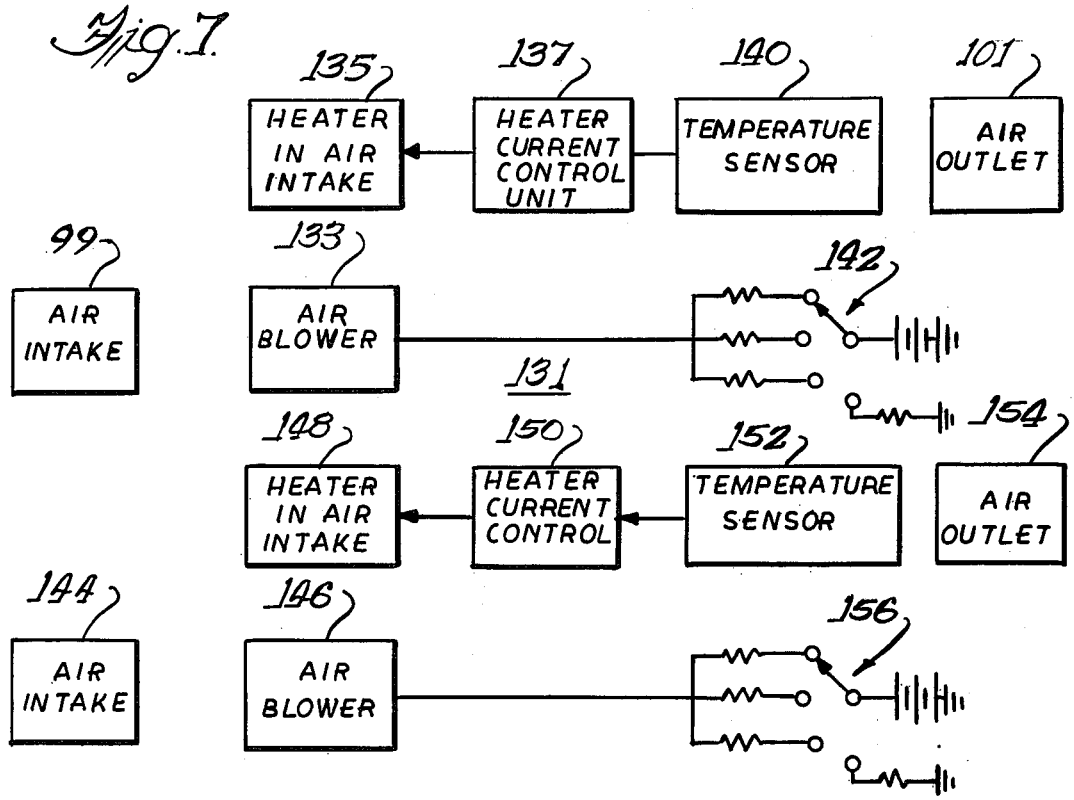
FIG. 7 is a block diagram of a temperature control system useful in an embodiment of the invention.

In FIG. 1, there is shown a chemical analyzer 10 having a base casing 12 in the form of a right-regular hollow parallelepiped and a back casing 14 having vertical parallel side walls, a vertical rear wall, a slanting front wall extending above the base casing 12 and top and bottom horizontal walls, with the back casing 14 and the base casing 12 together forming an L-shaped cabinet for the chemical analyzer 10.

Within the base casing 12, are an inner receptacle transport section, 16 (shown in FIG. 2), an outer receptacle transport section 18, and a C-shaped temperature control enclosure 20. The inner receptacle transport section 16 and the front portion of the outer receptacle transport section 18 are exposed to permit an operator to insert receptacles into and remove receptacles from them and the rear portion of the outer receptacle transport section 18 passes through the temperature control enclosure 20, thus not being directly accessible except by special measures.

To transport fluids from location to location within the chemical analyzer 10, a first plurality of the shuttles 22 are movably positioned to be driven within the inner receptacle transport section (shown in FIG. 2) 16 and a second plurality of the shuttles 22 are movably positioned to be driven in a circle within the outer receptacle transport section 18 with the shuttles 22 supporting chemical receptacles such as test tubes.

To control the temperature at which reactions occur in the fluids being transported by the shuttles 22 within the outer receptacle transport section 18, the C-shaped temperature control enclosure 20 has vertical walls extending above the base casing 12 adjacent to the back casing 14 and covered by a top wall, with a vertical entrance 24 and a vertical exit 26 facing the front of the analyzer 10 to permit the shuttles 22 within the outer receptacle transport section 18 to be moved into and from the temperature control section 20.

To transfer chemicals between the inner receptacle transport section 16 and the outer receptacle transport section 18, a chemical-transfer section 28 is located above the base casing 12 with one portion of it being adapted to extend through apertures 30 in the top of the temperature control enclosure 20 to communicate with chemical receptacles therein and with another portion of it being adapted to extend over the inner receptacle transport section 16, such as at 32 in FIG. 2.

The chemical-transfer section 28 is designed to include apparatus for: (1) transferring fluids into receptacles within the temperature control enclosure 20 from an external source; (2) transferring fluids in either direction between receptacles in the inner receptacle transport section 16 (shown in FIG. 2) and the outer receptacle transport section 18; (3) removing fluids from receptacles in either the inner receptacle transport section 16 or the outer receptacle transport section 18; and (4) treating fluids within receptacles in either the inner receptacle transport section 16 or the outer receptacle transport section 18 by methods such as stirring.

To mount the apparatuses for transferring or treating fluids in the outer transport section 18, the chemical transfer section 28 includes a horizontal flat elongated carrier arm 34 movably mounted by ears 36 to the back casing 14, with its longitudinal axis extending parallel to the longitudinal axis of the back casing 14 and its flat surfaces horizontal. To mount the apparatus for transferring and treating the chemical to the carrier arm 34, the carrier arm 34 includes a plurality of mounting apertures 38, with one of the apertures 38 receiving a first transferring and stirring device 40 and a second transferring and stirring device 42.

The first transferring and stirring device 40 includes an aspirating tube and a stir rod shown at 44 for insertion by downward movement of the carrier arm 34 through one of the apertures 38 into a receptacle within the temperature control enclosure 20 to stir the fluids therein or to withdraw fluids therefrom.

The second transferring and stirring device 42 similarly includes a stir rod and reagent tube shown at 84 (shown in FIG. 2) for movement through a different one of the apertures 38 into a receptacle within the temperature control enclosure 20 to insert a reagent or stir a chemical therein.

section 16 to the outer receptacle transport section 18, the chemical transfer section 28 includes a rotating sipper mechanism 48 having a rotatable post 50 and a sipper support arm 52, with one end of the sipper support arm 52 being mounted to the post 50 for rotation therewith and the other end 54 holding the upper end of a sipper so that the sipper orbits through an arc with an oscillatory motion as the post 50 rotates with an oscillatory motion. The sipper is inserted into a receptacle at each end of its arc between the inner receptacle transport section 16 and the outer receptacle transport section 18 to remove or insert a fluid. After the end 54 has orbited into position, the rotating post 50 is lowered to drop the sipper tube into the receptacle and then raised to remove the sipper tube from the receptacle before orbiting to a different position.

To monitor the operation of the chemical analyzer 10, a control panel 56 is mounted to the back casing 14 and has mounted to it facing forward for easy viewing and manipulation, indicator lights 58, electrical outlets 60, control switches 62 and a program card reader 63.

In FIG. 2, there is shown a fragmentary view of the chemical analyzer 10 broken away to expose the interior of the temperature control enclosure 20. As best shown in this figure, the shuttles 22 within the inner receptacle transfer section 16 and the outer receptacle transfer section 18 each support a different one of the receptacle holders 64, with the receptacle holders 64 being held on top of the shuttles by two posts 66A and 66B of the shuttles 22 for movement therewith.

In the inner receptacle transfer section 16, as best shown in FIG. 2, sample cups 68 are positioned over receptacles 69, with the sample cups 68 having a shallow central upward opening containing a small amount of reagent for insertion into receptacles within the outer receptacle transfer section 18 by the rotation sipper mechanism 48. In the outer receptacle transfer section 18, the receptacle holders 64 support incubation mixture tubes 72 which contain a reagent into which the sample that is being tested is inserted for incubation within the temperature control section 20.

While sample cups and incubation mixture tubes containing fluids to be processed within the chemical analyzer 10 have been shown in FIG. 2, it is obvious that other receptacles and fluids may be supported by the shuttles. Moreover, while one temperature enclosure 20 is shown, it is obvious that more than one enclosure may be included and other arrangements of reagent transferring and processing equipment may be utilized.

The inner receptacle transport section 16 includes a first transfer passageway 73 near the front of the base 12 having a forward end 75, a second transfer passageway 77 near the rear of the base 12 having a forward end 79, a forward shuttle magazine 81 (left-hand side as shown in FIG. 2) and a rear shuttle magazine 83 (left-hand side as shown in FIG. 1).

Similarly, the outer receptacle transport section 18 includes a first transfer passageway 85 near the front of the base 12 having a forward end 87 on one side, a rear transfer passageway 89 having a forward end 91, a forward shuttle magazine 93, and a rear shuttle magazine 95.

The forward ends of the outer transfer passageways are adjacent to the rearward ends of the inner transfer passageways, the forward magazine 93 of the outer receptacle transport section 18 being adjacent to the rearward magazine 83 of the inner receptacle transport section 16 and the forward magazine 81 of the inner receptacle transport section being adjacent to the rearward magazine 95 of the outer receptacle transport section 18, the shuttles 22 traveling in opposite directions in the inner and outer transport sections.

One of the shuttles in each of the transfer passageways is driven by a pinion that engages a rack on the bottom of the shuttles, and these shuttles pull or push the other shuttles into position, with the shuttles in the inner receptacle transport section 16 moving in a clockwise direction (as shown in FIG. 2) and the shuttles in the outer receptacle transport section 18 moving in a counter-clockwise direction. The arrangement of passageways and shuttle magazines is described more fully in U.S. Pat. No. 3,418,084 issued Dec. 24, 1968 to John R. Allington.

To control the temperature within the temperature control enclosure 20, the temperature control enclosure 20 includes a temperature control air inlet 99 at one end (right-hand side of FIG. 2) and an air outlet 101 on the opposite end. The temperature control enclosure 20 also includes temperature measuring devices to sense the temperature and to control heaters so that the temperature of the air is at a preset temperature within the temperature control section 20. More than one inlet and outlet may be utilized cooperating with partitions within the temperature control enclosure 20 to provide several sections having different temperatures if desired.

The receptacle holders 64 and the receptacles are of such a size that they substantially close the entrance 24 and exit 26 of the temperature control enclosure 20 thus permitting the temperature to be more easily maintained at the desired level. If partitions are desired within the temperature control enclosure 20, the walls only need extend from the bottom to the top of the temperature control enclosure and approach close to the path of the shuttles 22 since the receptacles extend from the bottom of the top of the container and are capable of sealing the openings through the partitions through which the shuttles pass.

As best shown in FIG. 2, the first transferring and stirring device 40 and the second transferring and stirring device 42 each include a different one of the stir rods 76 and 78 respectively. The first transferring and stirring device 40 also includes an aspirating tube 80 and a reagent tube 82 and the second reagent transfer and stirring device 42 includes a reagent tube 84.

When the carrier arm 34 moves downwardly, the stirring rods 76 and 78 on the first and second transferring and stirring devices, the aspirating tube 80 and the reagent tubes 82 and 84 are inserted into receptacles directly beneath them, with the stirring rods and aspirating tube being lowered to the bottom of the receptacle into the fluid therein while the reagent tubes are positioned near the top of the receptacles so that: (1) the aspirating tube is in position to draw the liquid upwardly from the receptacles; (2) the stir rods are in position to stir a fluid in the receptacles; and (3) the reagent tubes are in position to insert liquid into the receptacles.

To provide for the movement of liquids through the first and second transferring and stirring devices, the two flexible tubes 86 and 88 communicate respectively with the transferring and stirring devices 40 and 42, with the fluids being pumped therethrough by pumps (not shown in FIG. 2). The stirring rods are controlled by motors within the transferring and stirring devices 40 and 42, which are energized by a source of electricity (not shown).

In FIG. 3, there is shown in a plan view, one of the shuttles 22 having an elongated center body portion 90 with a tapered leading end 92 (right-hand side of FIG. 3) and a tapered trailing end 94 (left-hand side of FIG. 3), both the leading end 92 and the trailing end 94 having vertical walls sloping together to form the points 96 and 98 respectively. The point 96 is slightly offset to the right-hand side and the point 98 is slightly offset to the left of a center line 100 of the longitudinal body 90.

To hold the receptacle holders 64 and receptacles 69 (FIG. 2), the central portion of the elongated body 90 of the shuttle 22 includes two receptacle-receiving recesses 102 and 104 separated by a divider 106. At each end of the elongated body 90, a different one of the two support posts 108 and 110 extends upwardly from the recessed portion 102 or 104 at that end, the cylindrical support posts being slotted at their upper ends for a purpose to be described hereinafter.

In FIG. 4, there is shown a longitudinal sectional view of the shuttle 22, having a bottom surface with a plurality of gear teeth forming a rack 112 which engages with the teeth of a pinion 110. The upper surface of the trailing end 94 near the point 98 is recessed at 114 to form a hook member 116 extending upwardly, but not to the height of the walls of the shuttle 22. The leading edge 92 is formed in a reverse manner, having a downwardly-extending recess 118 and downwardly-extending hook member 126.

As shown in FIG. 5, the trailing edge 94 of the shuttle 22 includes upper tapered walls 122 and 124 reaching a point short of the point 98 of the shuttle and ending on a flat recessed surface at 114 (shown in FIG. 4) with the member 116 extending upwardly at the point 98 to a height lower than that of the top surface and being bound by the tapered side walls 128 and 130. The leading end 92 of the shuttle 22 is the same as the trailing end 94 shown in FIG. 5, but positioned upside down with respect to the trailing end 94.

In FIG. 6, there is shown, in perspective view, a receptacle holder 64 of the type shown in FIGS. 1 and 2, having an elongated plastic base 132 shaped in a manner similar to the outer walls of the shuttle 22 (FIG. 1) to fit thereover in coplanner relationship and having upstanding plastic portions 134 and 136, with the plastic portions 136 being larger in size than the plastic portions 134. In the center of each of the two end plastic portions 136 (one end being shown in FIG. 6), is a different cylindrical recess 138 extending upwardly from the bottom of the base 132 and of sufficient size to tightly receive the support posts 66 of a shuttle 22 (FIG. 1) to permit the receptacle holders 64 to be removably mounted to shuttles 22.

To hold receptacles, the upstanding plastic portions 134 and 136 have concave spaced-apart portions facing each other to enable receptacles such as test tubes to be inserted between two plastic portions 134 or 136 or two portions 136, and held in an upright position as the shuttles 22 are transported from one location to another.

In FIG. 7, there is shown a block diagram of a temperature control system 131 for controlling the temperature within the temperature control enclosure 20 having a first air blower 133 positioned near a first air inlet 99, an air heater 136 positioned in the air intake for the air blower 133, a first adjustable heater current control 137 for controlling the heat emitted by the air intake so as to set a predetermined temperature of the air, a first temperature sensor 140 positioned near the air outlet 101 within the temperature control enclosure 20, and a first air blower speed adjuster 142 for controlling the air blower 133.

Although the preferred embodiment of the chemical analyzer shown in FIGS. 1 and 2 requires only the above-described temperature control elements, FIG. 7 shows a duplicate of the above units for controlling two different enclosures for chemical analyzers having two such enclosures. The duplicate elements are a second air intake 144, a second air blower 146, a second heater 148 in the air intake 144, a second heater current control unit 150, a second temperature measuring device 152, a second air outlet 154, and a second air blower speed control 156.

The heater current control unit compares a signal from the temperature sensor and adjusts the heater in the air intake to maintain a preset temperature in response to the feedback signal from the temperature sensor. The air blowers 133 and 146 may be turned to different suitable speeds for use with the chemical analyzer. Of course, further units may be used to control further temperature control chambers where chemical analyzers are equipped with more than two temperature zones.

Figure 8:
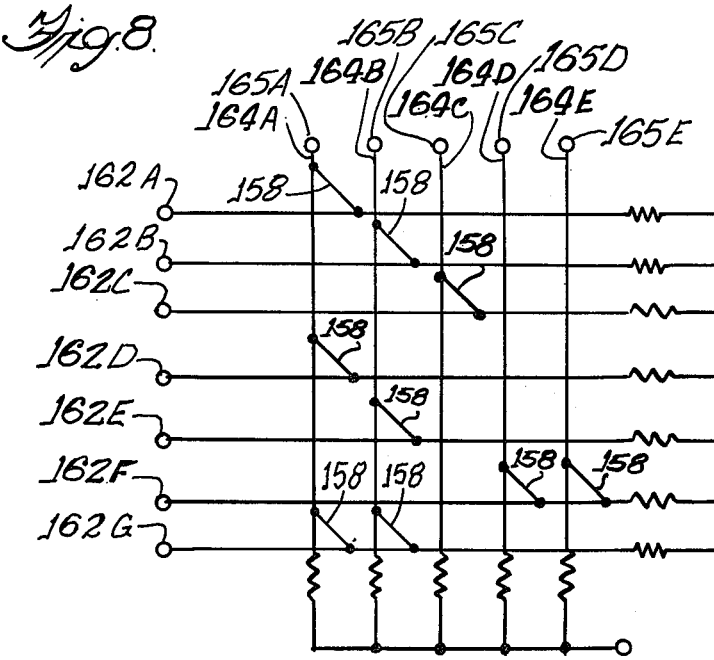
FIG. 8 is a simplified schematic circuit diagram of a program card useful in an embodiment of the invention.

To control the operation of the chemical analyzer 10, a selected program card containing conductive connecting plugs 158 (FIG. 8) cooperates with the program card holder 168 (FIG. 9), as best shown in FIG. 8, the program card having row conducters 162 and column conductors 164 to establish a program of operations in a chemical analyzer programmer 160, shown in a block diagram in FIG. 9. This program controls the motion of the shuttles 22, the sipper actuators, and the first and second reagent transfer and stirring units.

To provide different programs of operations which may be recycled continuously for the continuous operation of the chemical analyzer, selected ones of the row conductors 162 are connected to different ones of the column conductors 164 by conductive plugs 158, with seven row conductors 162A-162G and five column conductors 164A-164E being shown in FIG. 8 for purposes of explanation. In the preferred embodiment, twenty-two row conductors and twelve column conductors are included.

Certain selected ones of the row conductors represent certain commands which require quantitative information for their performance and other row conductors represent commands that do not require quantitative information. For example, a command to move the shuttles 22 until a different test tube is located under an aspirator does not require quantitative information whereas a command to pipette a reagent into a test tube does require quantitative information—the amount of the reagent to be pipetted into the test tube.

In the preferred embodiment, there are generally eight types of commands that are used, which are: (1) pipette a sample; (2) change tubes; (3) pipette a reagent; (4) time delay; (5) transfer contents of tube; (6) raise the pipette frame; (7) delay until clock recycles; and (8) go to step one.

To control the operation of the chemical analyzer 10 in response to the program on the program card, the programmer 160 includes a command interpreter 166, a program card holder 168, a logic section 170, a plurality of fixed-quantity step actuators 172, and a plurality of variable-quantity step actuators 174, as best shown in FIG. 9.

To sequence commands and data stored on the program card, row conductors 162A-162G of the program card holder 168 are connected to receive sequencing pulses from the logic section 170, with the column conductors 164A-164E being connected to corresponding ones of the terminals 165A-165E (FIGS. 8 and 10) to provide output pulses to the command interpreter 166 indicating the programmed command or quantity corresponding to sequencing pulses.

This type of arrangement enables a bus-bus type program card to be used without requiring isolation diodes, which is exceptionally economical for programming complex operations such as the operations necessary in an automatic chemical analyzer. By programming data after those commands which have variable data requirements, the program card is able to include a sufficient amount of information notwithstanding that many of the operations require the specification of particular quantities appropriate for the type of analysis being performed.

To interpret the command and the nature of the command, the command interpreter 166 includes a decoder which, upon receiving a signal from a column conductor 164 of the program card indicating a command, applies the command to the appropriate actuator in the group of fixed quantity step actuators 172 through a selected one of a plurality of conductors in the cable 180 or to the appropriate variable quantity step actuator in the variable quantity step actuators 174 through appropriate ones of the conductors in the cable 182. Data is applied to the variable quantity step actuators 174 through the cable 183 from the command interpreter 166.

To process variable quantity commands, the command interpreter 166 includes circuitry which cooperates with the logic section 170 to cause successive row conductors on the program card to receive pulses from the logic section 170 and to read first the appropriate command and then the corresponding data to the command interpreter 166 for application to the appropriate variable quantity step actuator in the group of variable quantity step actuators 174 through selected ones of the conductors in the cables 182 and 183, with the command output cables 180 and 182 being blocked while data is read from the program card into the cable 183.

To perform certain operations not requiring quantitative control such as raising the pipette frame or lowering the pipette frame, the fixed quantity step actuators 172 comprise a plurality of motor control units, each adapted to control a motor so that it moves an object such as the pipette frame a fixed distance and stops.

To perform operations that by their nature require quantitative control, such as the pipetting of a reagent, the variable quantity step actuators shown in the block 174 comprise a plurality of motor control units that control the operation of motor through a programmed distance, which may be accomplished by controlling some aspect of a motor such as the time the motor is running or the distance the moving portion of the motor moves or, in the case of pneumatic operation, the size of an opening or orifice or the like. For example, a typical variable quantity step actuator is a digital control which selects the limits of piston motion in a pipette and controls a motor to move the piston across only that distance so as to deposit a measured quantity of a reagent into a tube.

To provide for the sequencing of the fixed and variable quantity commands on the program cards, the logic unit 170 includes a clock 184, a control logic circuit 186, and a program counter 188 having a reset terminal 189, a count terminal 191 and a plurality of output terminals.

To provide the basic timing pulses that control the timing of the entire programming unit and the sequencing of commands, the timing clock 184 has its output electrically connected to the control logic circuit 186.

To energize different row conductors 162 of the program card to provide different commands to the column conductors 164 of the program card, the count input terminal 181 is electrically connected to the control logic circuit 186 and a plurality of output terminals are connected to the row conductors 162 in the program card holder 168. The control logic circuit 186 is interconnected with the fixed quantity step actuators 172 and the variable quantity step actuators 174 as well as with the program counter and the fixed and variable quantity command interpreter 166 and controls the sequencing of the program counter 188 in response to the completion of operations by the motors that are controlled by fixed and variable quantity step actuators 172 and 174.

In FIG. 10, there is shown a logic diagram of the command interpreter 166 having: (1) input terminals 165A-165E which are adapted to be connected to corresponding ones of the column conductors 164A-164E (FIG. 9) for receiving signals from the program card holder 168 (FIG. 9); (2) fixed quantity command output conductors 180A-180C for providing fixed quantity commands to the fixed quantity step actuators 172 (FIG. 9); and (3) variable quantity command conductors 182A-182C for providing variable quantity commands to the variable quantity step actuators 174 (FIG. 9); and (4) data conductors 183A-183C for providing data to the variable quantity step actuators 174.

The fixed and variable quantity command interpreter 166 includes circuitry that enables a predetermined number of input row conductors 162 (FIGS. 8 and 9); of a program card; (22 row conductors are actually present in the preferred embodiment) to be used with a smaller number of output column conductors 164 (12 column conductors are actually present in the preferred embodiment) and terminals 165 to which they are connected, with individual ones of the output conductors 164 being used for both a command and for data at different times to provide a larger number of output commands and data, without requiring a special design or isolation elements such as isolation diodes interconnecting the rows and columns of the program card to avoid sneak current paths even though the row conductors are, in some instances, electrically connected to more than one output terminal of the program counter 188 (FIG. 9) and are connected to more than one of the column conductors 164A-164E of the program card holder 168.

Because of the assignment of the output row conductors in the programming operation to carry fixed quantity commands, variable quantity commands or data, the programmer 160 has low operating time and is inexpensive since the number of busses is reduced and diodes or other isolation elements between rows and columns of the program card are unnecessary.

The fixed and variable quantity command interpreter 166 can be used with standard commercial program card holders or apparatuses and standard program cards such as those manufactured by Sealectro Corporation, Manaroneck, New York, and designated MBR series punched badge, mini-badge readers and badges. The basic structure of suitable program cards and holders are also described in U.S. Pat. Nos. 3,476,983 and 3,373,319.

To provide the fixed quantity step commands to the fixed quantity step actuators 172, the command interpreter 166 includes NAND gates 194A-194F, a command request input conductor 204, an inverter 200 and a conductor 206, with five of the NAND gates 194A-194E, being electrically connected to a corresponding one of the output conductors 164A-164E (FIG. 8) through corresponding terminals 165A-165E (FIG. 10) and row conductors 178A-178E, the other input terminal of each being electrically connected to receive a command request signal on conductor 206 from the inverter 200 in response to a signal on conductor 204. The output of NAND gates 194A-194E are electrically connected to a corresponding one of the output conductors 180A-180C or 182A-182B.

To increase the number of fixed commands available from the fixed and variable quantity command interpreter 166 further without increasing the number of output row conductors 162 of the program card (FIG. 8), there is included in the fixed and variable quantity command interpreter 166 a logic-developed command circuit 190 having a NOR gate 192 and a NAND gate 194F. The logic-developed command circuit 190 cooperates with the NAND gates 194A–194E to provide an additional fixed quantity command output on conductor 182C, and the last program step also initiates a go to step one command at its termination to provide still another command extending the 22 outputs of the program card used in the preferred embodiment to 24 commands.

To provide the additional fixed quantity command, each of the row conductors 164A–164E (FIG. 8) is electrically connected to a different one of the input terminals of the NOR gate 192 through corresponding terminals 165A–165E so that the NOR gate 192 provides a binary-0 or a low-potential output each time it receives a high-potential or a binary-1 output from any one of the row conductors 164A–164G. The output of the NOR gate 192 is connected to one of the two inputs of the NAND gate 194F, with the output of the NAND gate 194F being connected to receive a binary-1 or a high-potential signal each time a fixed-quantity command is requested.

The NOR gate 192 applies a binary-1 to one of the inputs to gate 194F any time a command is requested, but the program card holder 168 (FIG. 8) has no row input conductor connected to a column output conductor, thus causing the NAND gate 194F to provide a binary-0 to the conductor 182C, which binary-0 is used to control an actuator in the group of actuators 174 (FIG. 9). Accordingly, one fixed actuator is programmed to be energized without an output row conductor on the program card being needed by causing a command request signal to be generated in the normal manner at some particular output of the program counter 188 with no connection between that output and an output of the program card and by connecting conductor 182 to the actuator that is to be energized by the binary-0 signal.

With these connections, whenever a command signal is generated in a manner to be described hereinafter, a binary-0 command is provided to a programmed one of the conductors 180A–180C and 182A–182C corresponding to one of the outputs from the program card 168 or from the logic-developed command circuit 190. The binary-0 is applied to the selected one of the conductors 180 or 182 because the corresponding one of the NAND gates 194A–194F receives a binary-1 from a corresponding one of the conductors 178A–178F together with a binary-1 indicating a command.

To provide data, the command interpreter 166 includes five data conductors 196A–196D, a decoder 198, and the data output conductors 183A–183C. Each of the five conductors 196A–196D is electrically connected to a corresponding one of the output conductors 164A–164E along its length, to the NOR gate 192 at one end and to the decoder 198 at its other end, with the decoder 198 decoding the signals on conductors 196A–196D representing data and applying them to conductors 183A–183C.

The inverter 200 receives a binary-one on conductor 204 indicating a variable quantity command request in the previous program step and applies a binary-zero on conductor 206 in response to the signal to each of the NAND gates 194A–194F to inhibit fixed command outputs on conductors 180A–180C and 182A–182C during the time data is being provided from the decoder 198 through conductors 183A–183C. Of course, a decoder is not necessary in embodiments in which the output from conductors 196A–196E is of the type suitable for providing data to the variable quantity actuators.

Figure 11:
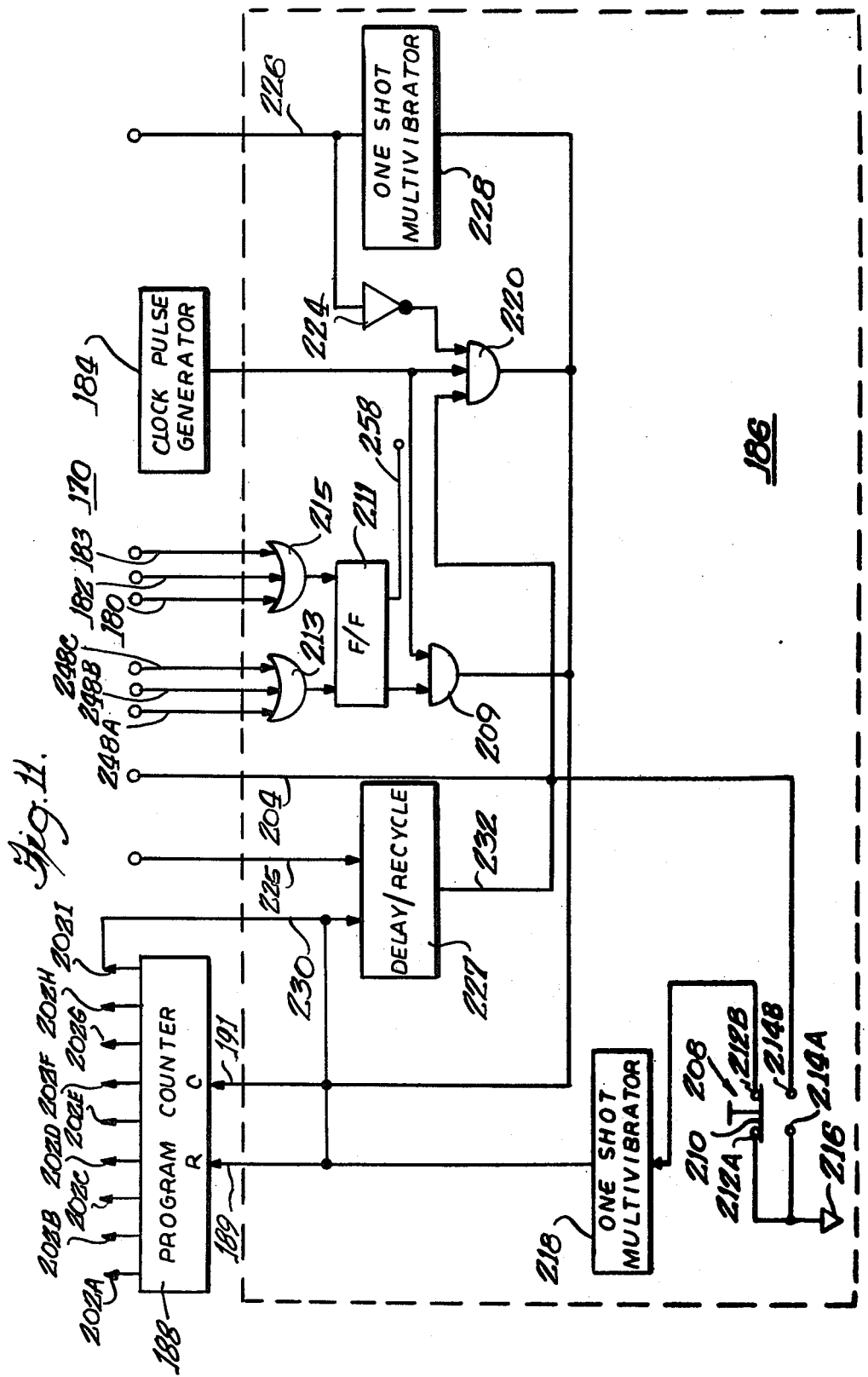
FIG. 11 is a block diagram of a control logic circuit which is a portion of the programming system shown in FIG. 9 in accordance with an embodiment of the invention.

In FIG. 11, there is shown a block diagram of the logic section 170 having the program counter 188, the clock pulse generator 184, and the control logic circuit 186. The clock pulse generator is a source of 50 or 60 Hz. pulses and is connected to the control logic circuit 186 to provide timing pulses thereto, with the control logic circuit 186 being connected to the actuators, some of the units controlled by the actuators, the program counter 188, and the command interpreter 166 (shown in FIG. 99) to receive further signals indicating the completion of operations of the actuators and to control the program counter 188 and command interpreter 166.

To sequence the program card (FIG. 8) within the program card holder (FIG. 9), the program counter 188 includes a plurality of output conductors, nine such conductors 202A–202I being shown in FIG. 11 for purposes of illustration. It also includes a clock pulse input conductor 191, and a reset input terminal 189.

Although nine output conductors 202A–202I connected to nine output terminals are shown in FIG. 11 for the program counter 188, the preferred embodiment includes twenty-four such conductors, which is sufficient to provide one output for each command and an output to control recycling of the commands.

The outputs for the commands include one command, which is programmed by the absence of a connection on the program card and which is applied to output conductor 182C (FIG. 10) as explained above. With this structure, each time a clock pulse is applied to the conductor 191 by the control logic circuit 186 from the clock 184, a different one of the output conductors 202A–202I is energized to step from position to position of the program card holder 168 resulting in a sequence of the commands. The reset conductor 189 is energized by the control logic circuit 186 to start a new cycle, which may be accomplished manually or automatically.

To coordinate the sequencing of the program counter 188 with the other units in the chemical analyzer 10, the control logic circuit 186 includes circuitry that: (1) manually starts a cycle of operation; (2) automatically recycles the program to perform chemical analysis on a series of samples; (3) delays the sequencing until certain operations have been completed; and (4) synchronizes the operation of units.

To manually start a cycle, the control logic circuit 186 includes a push-button switch 208 having an armature 210, a first pair of stationary contacts 212A and 212B and a second pair of stationary contacts 214A and 214B. The armature 210 normally connects contacts 212A and 212B and the source of positive potential 216 is electrically connected to fixed contacts 212A and 214A. Stationary contact 214B is electrically connected to the three-input AND gate 220 and to conductor 204, with AND gate 220 having a second input electrically connected to the clock pulse generator 184, a third input connected to conductor 226 through inverter 224, and an output connected to pulse input terminal 191 for the program counter 188. The fixed control 212A is electrically connected to the source of power 216.

Conductor 204 is connected to: (1) inhibit line 206 through inverter 200 (FIG. 10) in the command interpreter 166 to delay operation of the actuators until the push-button switch 208 is released; and (2) to the variable quantity step actuators 174 (FIG. 9) to cause data to be read into the delay data latches in the actuator, which delay data latches are described hereinafter. A selected output of the command interpreter 166 (on conductor 226 in FIG. 11) is connected to the AND gate 220 through an inverter 224.

To reset the program counter 188 when the push-button switch 208 is released and thus electrically connect 212A and 212B together, contact 212B is electrically connected to the reset conductor 189 through a one-shot multivibrator 218 and contact 212A is connected to a source of potential 216.

With these connections, when the push-button switch 208 is depressed, two operations take place and when it is released, one other operation takes place.

Firstly, when it is depressed: (1) a pulse is applied to conductor 204 which causes data to be read into the delay data latches of the actuators and inhibits the actuators; and (2) a pulse is applied to AND gate 220, opening this gate and causing the program counter to begin stepping at a 50 or 60 Hz. rate to a predetermined position at which position a delay command is provided to conductor 226 from the program card through the command interpreter 166. The delay command is programmed at one position of the program card which position is one step before the start position of the program.

To initiate a delay, this delay command pulse is applied to AND gate 220 through inverter 224 from conductor 226 and causes the AND gate 220 to open, thus stopping sequencing of the program counter 188. The one-shot multivibrator 228 also receives this pulse from conductor 226 and generates another pulse which is applied through conductor 191 to step the program counter one further position at which position a pulse is provided to conductor 204 to inhibit reading of gates 194 (FIG. 10) and to read data into conductors 183 to the variable command actuators. When the push-button switch 208 is released, a pulse is applied through the one-shot multivibrator 218 to reset the program counter to its position-one for further sequencing.

To automatically recycle the program, the control logic circuit 186 includes a delay/recycle unit 227 having a data input cable 225, a control input conductor 230, and an output conductor 232, with the control input conductor 230 being connected to the final terminal 202I of the program counter 188 and to the reset terminal of the program counter 188 to start the delay/recycle unit 227 upon energization of the final output terminal 202I of the program counter 188 and to reset the program counter 188. An amount of delay time is set into delay/recycle unit 227 through conductor 225 and after this delay the electrical conductor 232 opens gate 220 to start a new cycle with the stepping of the program counter 188 to the load initial data step.

To delay further sequencing of the program until operations have been completed, the control logic circuit 186 includes an AND gate 209, a flip-flop 211, a first OR gate 213, and a second OR gate 215, with the output of the AND gate 209 being connected to conductor 191, one of its two inputs being connected to the clock pulse generator 184 and its other input being connected to the set output terminal of the flip-flop 211 so that when the flip-flop 211 is set, clock pulses are applied through the AND gate 209 to the count terminal of the program counter 188 for sequencing of the program and when the flip-flop 211 is reset, the pulses from the clock pulse generator 184 are blocked.

To sequence to a new command, the output of the OR gate 213 is connected to the input terminal of the flip-flop 211 and its inputs are connected to the actuators 172 and 174 to receive signals indicating the end of an operation so that the flip-flop 211 is set to permit a clock pulse from the clock pulse generator 184 to be passed to the count terminal by the conductor 191 upon completion of an operation.

To prevent sequencing during the operation by an actuator, the OR gate 215 has its output connected to the reset terminal of the flip-flop 211 and its inputs connected to the command of inputs of the fixed quantity step actuators 172 and the data inputs of variable quantity step actuators 174 through cables 180 and 183 respectively so that when a pulse is received from the command interpreter 166 to initiate an operation by an actuator, the flip-flop 211 is reset to prevent further sequencing by closing the gate 209 to clock pulses from the clock pulse generator 184. The complements output of flip-flop 215 is applied to inhibit line 258 to indicate that an actuator is in operation.

Figure 12:
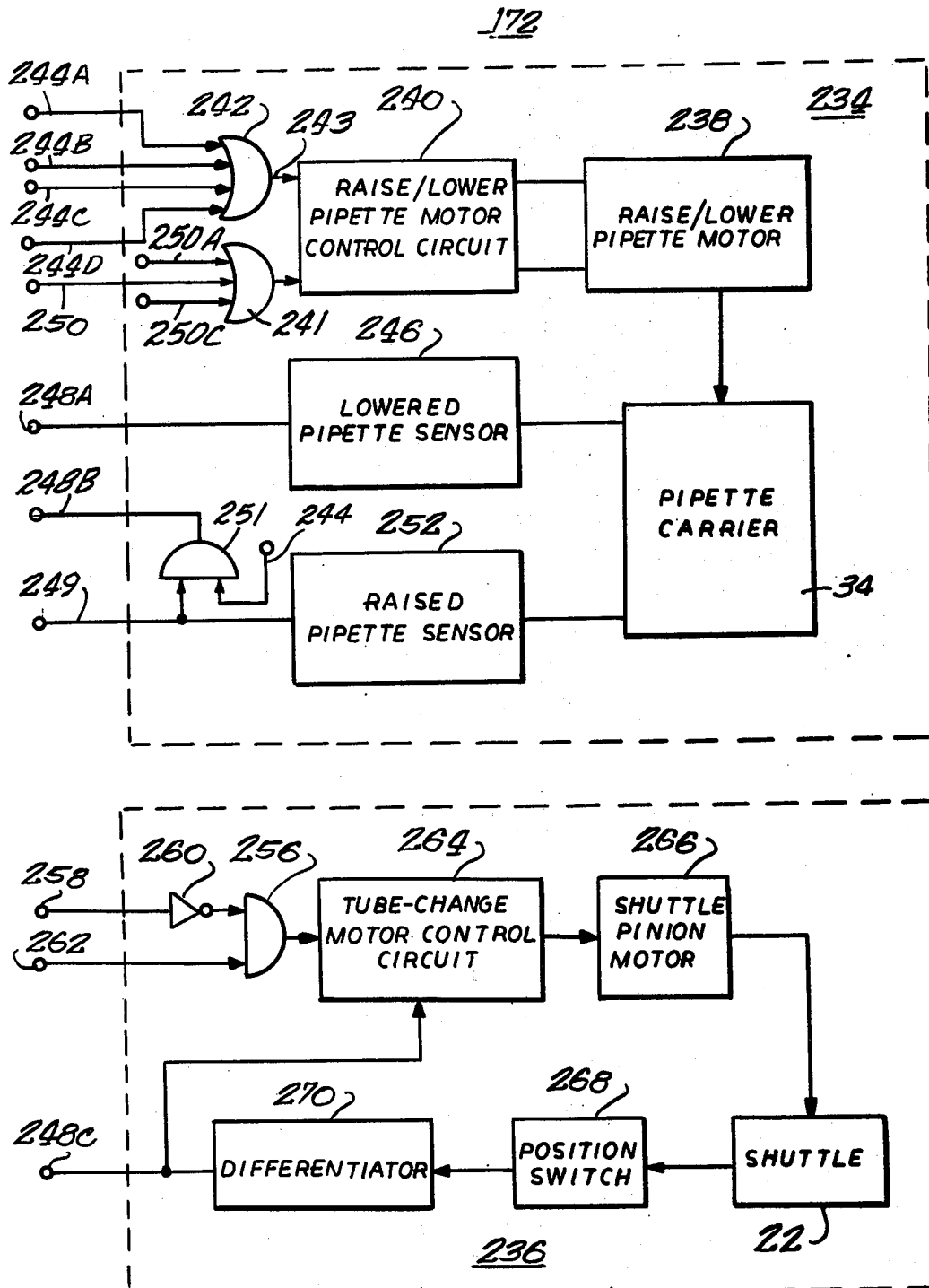
FIG. 12 is a block diagram of certain fixed step actuators that may be controlled by the programming system shown in FIG. 9.

In FIG. 12, there is shown a block diagram of the fixed quantity step actuator 172 including a raise/lower pipette-carrier actuator 234 and a move-to-one-position actuator 236, each of which performs functions not requiring variable data.

To raise and lower the pipette carrier arm 34 (FIG. 1), the raise/lower pipette-carrier actuator 234 includes a reversible raise/lower pipette motor 238 mechanically connected to the pipette carrier arm 34 and electrically connected to a raise/lower pipette motor control 240. The pipette motor 238 and motor control 240 cause the pipette carrier arm to be raised or lowered between fixed limits at the appropriate time.

To cause the raise/lower pipette motor control 240 to be lowered to insert pipette tubes into test tubes within the racks, an OR gate 242 has its output electrically connected to the lower pipette input terminal of the raise/lower pipette motor control circuit 240 and has a plurality of input conductors 244A–244D, certain of which are connected to different ones of the output conductors 180 (FIG. 10) from the command interpretor 166 so that the pipette carrier arm 34 is lowered whenever the command interpreter provides a command requiring the insertion of a reagent or the transfer of the liquid from a tube to another location to one of the conductors 180A–180C and others of which are connected to sensors in the variable step actuators to lower the pipette when necessary for other operations.

A sensor 246, such as a Microswitch push-button switch, is positioned to be energized when the carriage is fully lowered so as to apply a signal to output conductor 248A that: (1) prevents the reagent from being deposited too soon into a tube; (2) prevents an aspirator from attempting to withdraw a fluid before the pipette carriage is fully lowered; and (3) controls the distance through which the carriage is to be lowered. The signal on conductor 248A also initiates the next operation for which the carriage has been lowered.

To raise the pipette carrier arm 34, an OR gate 241 has its output electrically connected to the raise pipette input terminal of the raise/lower pipette motor control circuit and has a plurality of input conductors 250 which receive signals at the end of an operation from other units and apply these signals through the OR gate 241 to the raise/lower pipette motor control 240 to cause the raise/lower pipette motor 238 to move in an upward direction and carry the pipette carrier arm 34 with it. To sense when the pipette carrier arm 34 is fully raised and to initiate further operations, a Microswitch 252 senses the fully-raised pipette and applies a signal to conductor 249 and to one of the two inputs to AND gate 251. The other input to AND gate 251 is connected to certain of the conductors 244 and the output of AND gate 251 is connected to conductor 248B to provide a new raise pipette command signal.

To move the tubes in the outer receptacle transport section 18 one position at a time, the actuator 236 includes an AND gate 256 having a first input electrically connected to a conductor 258 through inverter 260 and a second input electrically connected to conductor 262, the output of the AND gate 256 being connected to a tube change motor control unit 264. The tube change motor control unit 264 drives the shuttle pinion drive motor 266 to move the shuttles 22 in a circular path in the outer receptacle transport section 18 (FIG. 1) until a position switch 268 senses a new tube.

The position switch 268 generates a pulse and applies it to a differentiator 270 which differentiates the pulse, applying it to output conductor 248C and to a input terminal of the tube change motor control unit 264 to stop the motor 266. When another operation is being performed, a signal is applied to AND gate 256 through an inverter 260 from conductor 258 to inhibit movement of the shuttles.

While only two actuators 234 and 236 have been described as fixed quantity actuators in the description of the preferred embodiment, more or fewer actuators may be included in other embodiments without deviating from the principles of the invention. For example, a sample pipette actuator, which is a variable quantity actuator in the preferred embodiment, in other embodiments may be a fixed quantity actuator provided the same quantity of a sample is always to be supplied to the tubes.

Moreover, while the actuator 236 has been described as a fixed quantity actuator in the description of the preferred embodiment, a variable quantity actuator or both a fixed and a variable quantity actuator may be included instead in other embodiments, with the fixed quantity actuator being used to move shuttles within the central transport path 16 and the variable quantity actuator being within the outer transport path 18. A variable quantity actuator would be used in embodiments in which different tubes are to be moved through different length paths to provide longer reaction times for some reagents than for others.

Figure 13:
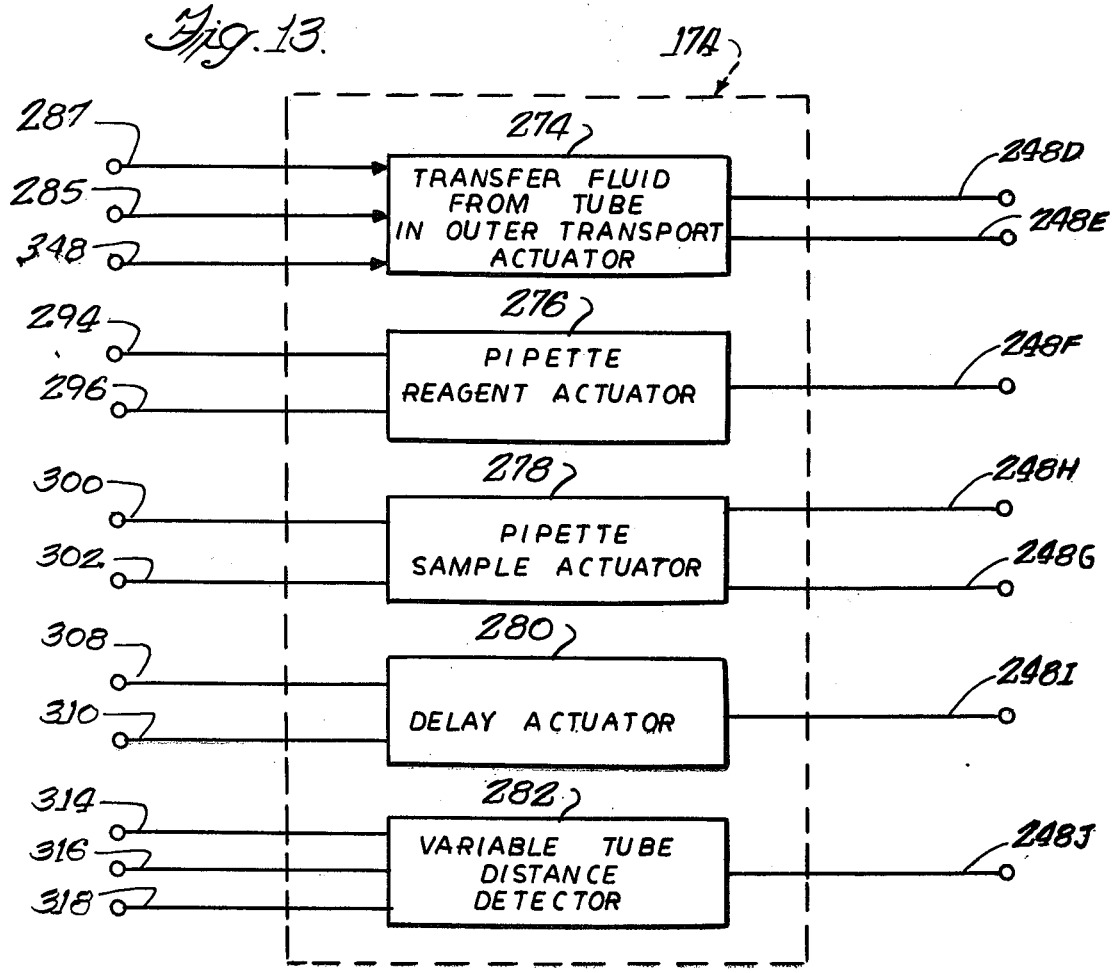
FIG. 13 is a block diagram of certain variable quantity actuators used with the programming system shown in FIG. 9.

In FIG. 13, there is shown a block diagram of the variable quantity actuators 174 having a transfer fluid actuator 274, a pipette reagent actuator 276, a pipette sample actuator 278, a delay actuator 280, and a variable distance mover actuator 282.

To transfer fluid from a tube into a measuring and readout instrument such as standard spectrophotometer-printout combinations, the transfer fluid actuator 274 has three input conductors 287, 285 and 348 which receive respectively a transfer command, a completed printout signal, and data information. Two output conductors 248D and 248E, provide a start transfer signal for inhibiting purposes and a quantity readout signal respectively.

To deliver reagents into test tubes, the pipette reagent actuator 276 includes two input conductors 294 and 296, the first of which receives signals from the command interpreter 166 (FIG. 10) indicating that a reagent command has been provided and the second of which receives a lower pipette carrier signal from conductor 248A (FIG. 12). A single output conductor 248F provides a signal generated by the actuator 276 indicating the end of the reagent pipetting operation.

To pipette a sample, the pipette sample actuator 278 includes two input conductors 300 and 302, with one of the input conductors receiving a lower carrier signal from conductor 248A (FIG. 12) and the other receiving a pipette command from the command interpreter 166 (FIG. 10), and two output conductors, one output conductor 248G providing a finish pipetting sample signal and a second output conductor 248H indicating the sample tube is over the sample container.

To provide a variable delay time signal, the delay actuator 280 includes a variable time delay having a first input conductor 308 which receives the start signal, a second input conductor 310 which receives data indicating the amount of time delay and an output condutor 248I which indicates the end of the time delay period.

To provide a variable distance of motion for tubes, a variable distance mover actuator 282 includes a first input conductor 314 which receives an end of operation signal, a second input conductor 316 which receives a command signal, a third input conductor 318 which receives a variable distance signal, and an output conductor 248J, which provides an end of motion signal.

Figure 14:
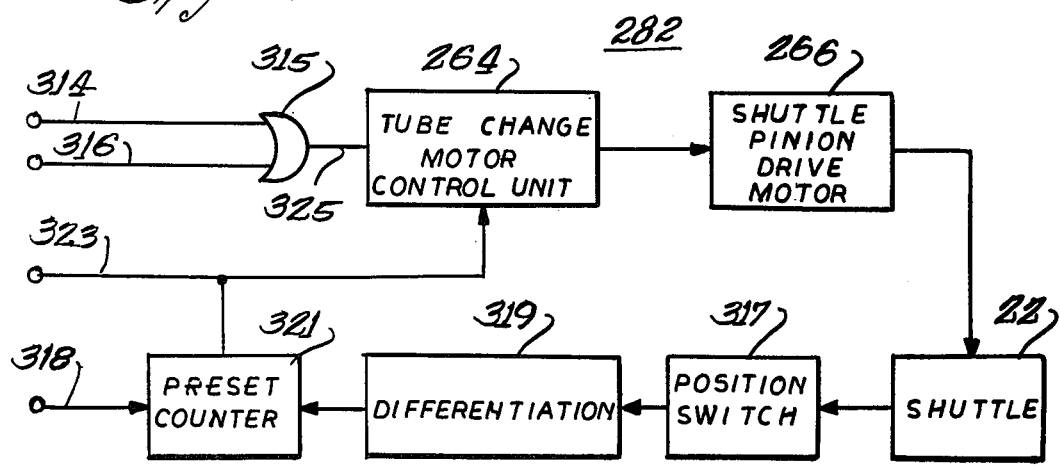
FIG. 14 is a block diagram of one of the variable quantity actuators shown in FIG. 13.

In FIG. 14, there is shown a block diagram of a variable distance mover actuator 282 which may be used in place of one or more of the fixed distance mover actuators 236, one of which is shown in FIG. 12. The variable distance mover actuator 282 includes some of the same parts as the fixed distance mover actuator 236 and these parts include the same reference numerals.

The variable distance mover actuator 282 includes an ANd gate 315, a tube change motor control unit 264, a shuttle pinion drive motor 266, a shuttle 22, a position switch 317 which may be a Microswitch push-button switch or photocell combination arranged to detect the position of the shuttles 22, a differentiator 319, and a presetable counter 321.

The AND gate 315 has its two inputs connected to conductors 314 and 316 and thus provides a signal to its output conductor 325 whenever the previous operation is completed and a command is provided for a variable distance mover with the conductor 325 being electrically connected to the tube change motor control unit 264 to start the shuttle pinion drive motor 266 which moves the shuttles 22.

Each time a shuttle 22 is moved one position, the position switch applies a pulse to the preset counter 321 through the differentiator 319. The preset counter 321 receives data on conductor 318 indicating the number of tube positions through which the shuttles 22 are to be moved and applies a signal to the tube change motor control unit 264 through conductor 323 after this number of positions has been moved causing it to be counted to its output by pulses from the differentiator 319. This signal stops the shuttle pinion drive motor 266.

The variable distance mover actuator is not included in the preferred embodiment but may be included in any embodiment in which tubes are to be moved different distances under different circumstances.

Figure 15:
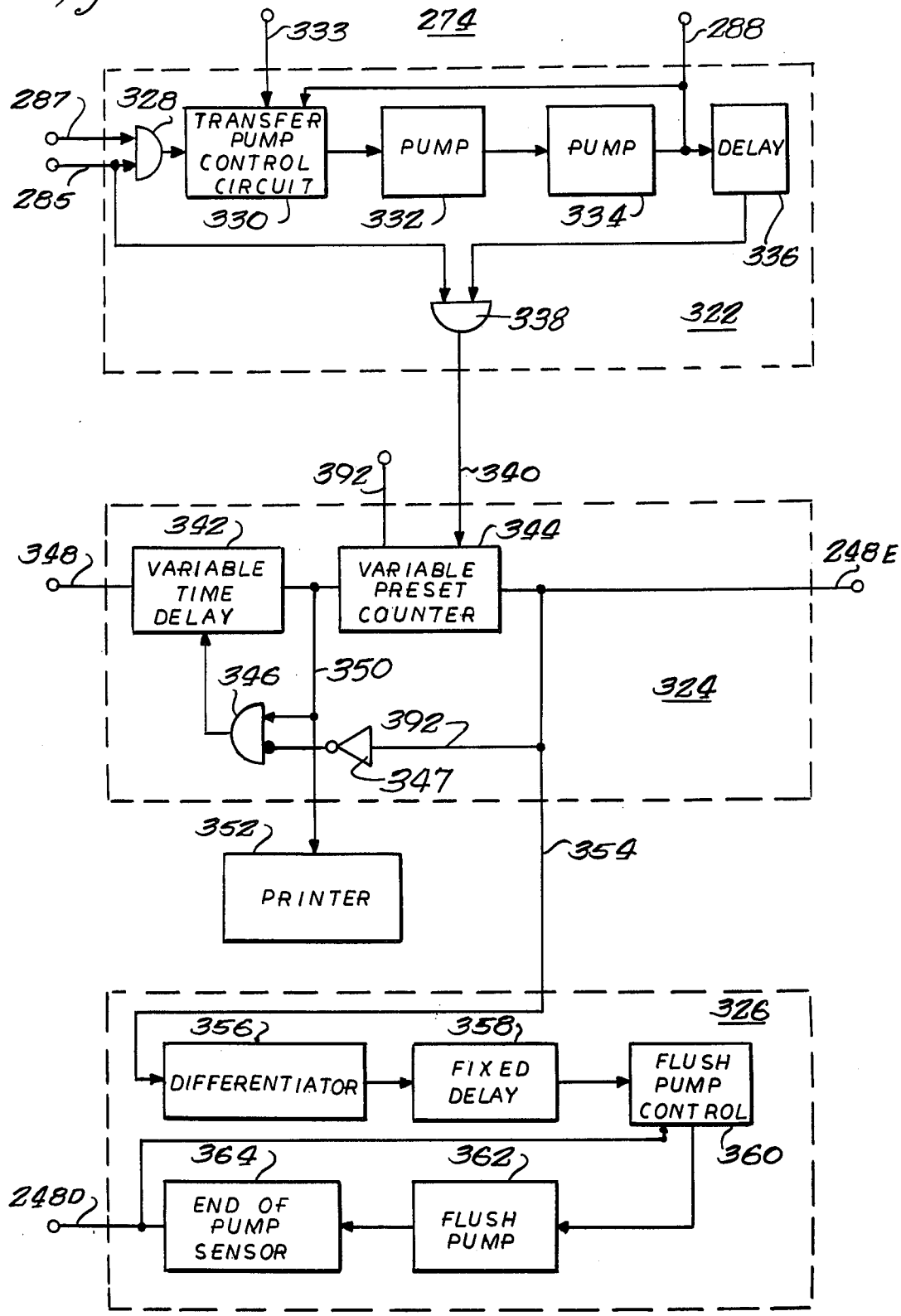
FIG. 15 is a block diagram of another variable quantity actuator shown in FIG. 13.

In FIG. 15, there is shown a block diagram of the transfer fluid actuator 274 which transfers fluids to a recording spectrophotometer having for this purpose a pump control section 322, a printer control section 324, a pump purging control system 326 and a printer 352.

To control the pumping of the fluid into the spectrophotometer, the pump control section 322 includes a two-input AND gate 328, a transfer pump control circuit 330, a transfer pump 332, a pump position sensor 334, a delay 336, and a second AND gate 338, with the AND gate 328 receiving the lower position carrier signal on a conductor 287 from the lower pipette sensor 246 (FIG. 12) and the transfer command signal on a conductor 285 from the command interpreter 166 and applying its output to the input of the transfer pump control unit 330 upon receiving these two signals to start the pump 332 which is controlled by the transfer control unit 330.

The pump position sensor 334 senses when the pump 332, which may be a syringe, reaches its end position and applies the signal to conductor 288 to delay line 336 and to the transfer pump control unit 330 to indicate the end of the pumping cycle, to turn off the pump motor 332 and to apply a signal after a delay controlled by the time delay 336 to one of the inputs of the AND gate 338. The other input of AND gate 338 originates with conductor 285 indicating a transfer command, causing the output of the AND gate 338 to be applied to the printing control section 324 through conductor 340 after the delay 336 to permit reading by the spectrophotometer.

To control the printing of information from the spectrophotometer, the print control section 324 includes a variable time delay clock 342, a variable presettable counter 344, an AND gate 346 and an inverter 347. The variable time delay 342 receives programmed time delay data from the command interpreter 166 (FIG. 10) on conductor 348 and after this time has elapsed, provides periodic pulses to the count input terminal of a variable preset counter 344 and to one of the inputs of the AND gate 346 through conductor 350, the other input to the AND gate 346 being connected to the output of the variable preset counter 344 through an inverter 347, so that a signal is provided by the AND gate 346 to the variable time delay at the end of the counting period for the variable preset counter 344 to terminate the generation of pulses in the variable time delay clock 342. The input of conductor 350 is applied to the printer 352 to cause a printout at regular periods of time.

To stop the printer 352, the variable preset counter 344 receives programmed data indicating a period of time for the entire readout on conductor 392 and applies a pulse to its output at the end of that period of time to open AND gate 346 and apply a pulse to the pump flush section 326 through conductor 354.

To flush the residue of the fluid from the pump before another analysis is made, the pump flushing circuit 326 includes a differentiator 356, a fixed time-delay unit 358, a flush pump control unit 360, a flush pump 362, and an end-of-flush signal generator 364. The differentiator receives a signal on conductor 354 from the variable preset counter 344 indicating the end of the reset, differentiates this signal and applies it to the flush pump control 360 through the fixed time delay 358 to cause the flush pump 362 to begin a flushing operation a period of time after the final printout. The flush pump 362 continues this operation until the end-of-flush signal generator 364 senses the end of the time period and applies a signal to the end of the transfer conductor 248D and to the flush pump control 360 to stop the flushing operation and to provide an indication that the transfer operation is complete.

Figure 16:
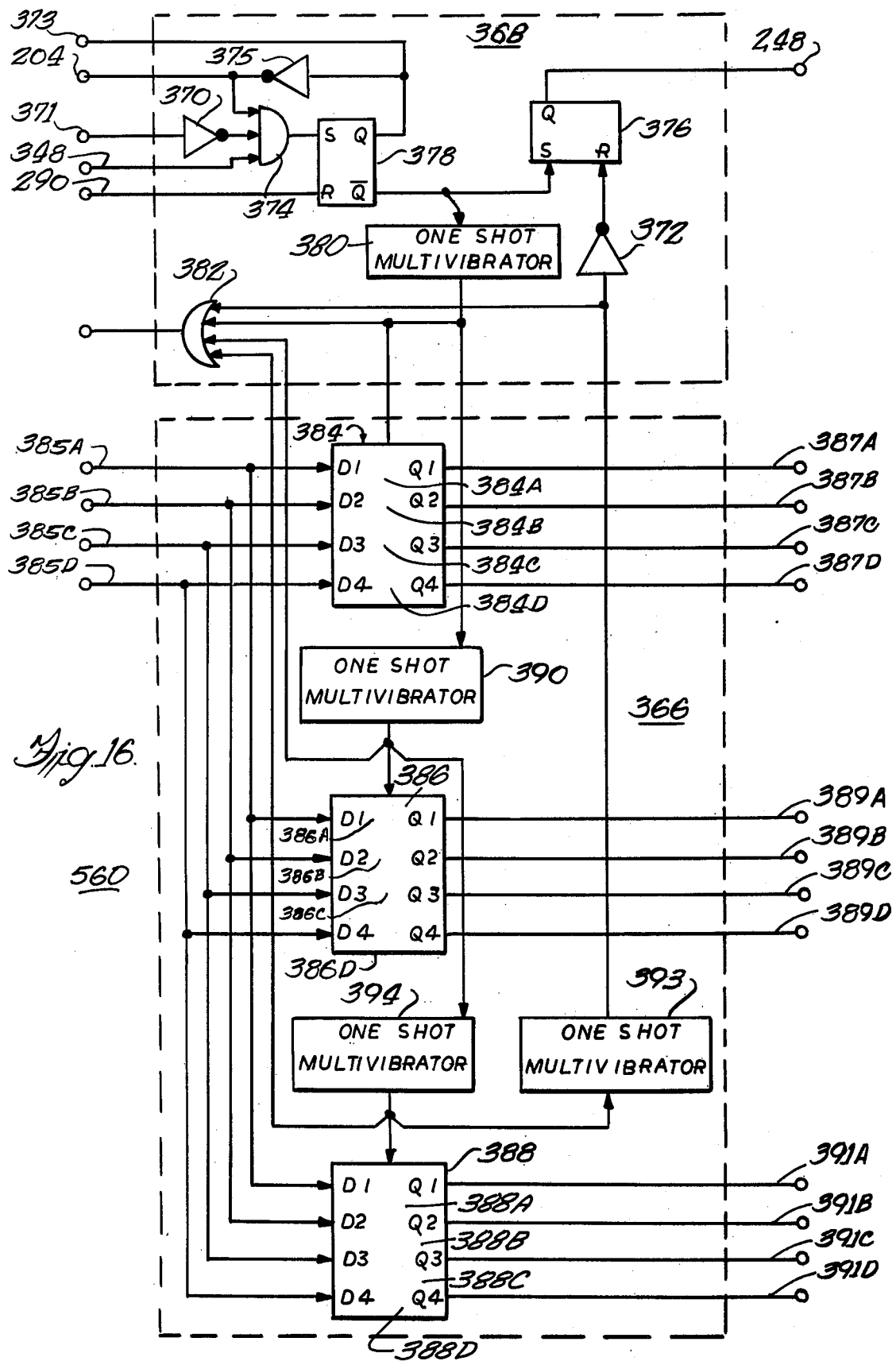
FIG. 16 is a memory circuit included in the programming system of FIG. 9.

In FIG. 16, there is shown a memory circuit 560 usable with any of the variable command actuators that require the storage of input data, but is particularly useful as a memory section within the transfer pump control unit for storing data.

To store data, this circuit includes a storage section 366 and a control section 368.

The control section 368 includes three inverters 370, 372 and 375, a NAND gate 374, two flip-flops 376 and 378, a one-shot multivibrator 380 and an OR gate 382.

To select the time for reading into the memory, the NAND gate 374, has its output connected to the set terminal of the flip-flop 378, a first of its three inputs electrically connected through the inverter 370 to terminal 371, which receives transfer commands from the command interpreter 166 (FIG. 10), a second input electrically connected to the completed operation signal conductor 348 for the spectrophotometer, and its third input connected to the output of inverter 375 through conductor 204.

With this arrangement, the flip-flop 378 is set upon the coincidence of a binary-0 transfer command, a completed operation signal and a signal indicating that data is not being transferred, with the output of the flip-flop 378 providing a start transfer signal to terminal 373 and an inhibit command signal to terminal 204 through inverter 375 with terminal 204 being connected to one of the inputs of NAND gate 374 to open this gate. The reset input terminal of flip-flop 378 is electrically connected to the transfer complete input signal line 290 to reset the flip-flop 378 upon the completion of a transfer operation.

To permit the entry of information into the proper location in the storage section 366, the complement output terminal of flip-flop 378 is electrically connected to the set input terminal of the flip-flop 376 and to the one-shot multivibrator 380, the output of the one-shot mutivibrator 380 being connected to the OR gate 382 and to the first register of the register 384 in the storage section 366 to cause data to be written into the first register.

The output of flip-flop 376 is connected through conductor 248 to an input of the OR gate 213 (FIG. 11) to step the program counter to the data write position and thus serves as a data write command. The reset input terminal of the flip-flop 376 is electrically connected to the storage section 366 through the inverter 372 to reset the flip-flop 376 for further control of the entry of data to the storage section 366 when the last register is full.

The storage section 366 includes a plurality of separate registers 384, 386 and 388 and a plurality of one-shot multivibrators 390, 393 and 394, with the registers 384, 386 and 388 each having four different storage stages 384A–384D, 386A–386D and 388A–388D respectively. Four input conductors 385A–385D are connected to corresponding ones of the four stages in each of the registers 384, 386 and 388 in parallel and corresponding ones of the conductors 387A–387D, 389A–389D, and 391A–391D are connected to different ones of the stages 384–384D, 386A–386D and 388A–388D respectively.

To write data sequentially into the registers 384, 386 and 388, the outputs of the one-shot multivibrators 380 (control section 368), 390, and 394 (storage section 366) are connected to the enable input terminals of the registers 384, 386 and 388 respectively and to the inputs of the multivibrators 390, 394 and 393 respectively, with the output of the multivibrator 393 being connected to the input of the inverter 372 (storage section 366) and the outputs of each of the four multivibrators 380, 390, 394 and 393 each being connected to a different one of the four inputs of the OR gate 382.

With this arrangement, the one-shot multivibrator 380 in the control section 368 is triggered by the complementary output of the flip-flop 378 and in turn: (1) enables the register 384 to accept data and at the same time apply a signal to the OR gate 382, thus causing data to be written into the register 384; and (2) triggers the one-shot multivibrator 390. After data has been written into the register 384, the one-shot multivibrator 390, having been triggered by the output of the one-shot multivibrator 380, applies a signal to the enable gate of the register 386 and the OR gate 382 to cause the next set of data to be written in parallel into the register 386 and applies a signal to the one-shot multivibrator 394. The one-shot multivibrator 394, having been triggered by the output of the one-shot multivibrator 390, enables the register 388 and applies a signal through the OR gate 382 to cause data to be written into the register 388 and triggers the one-shot multivibrator 393, which resets the flip-flop 376 to terminate the transfer of data.

This sequential generation of pulses by the monostable multivibrators provides for a series of writing and readout of data by the sequential triggering of the terminals of the registers.

Figure 17:
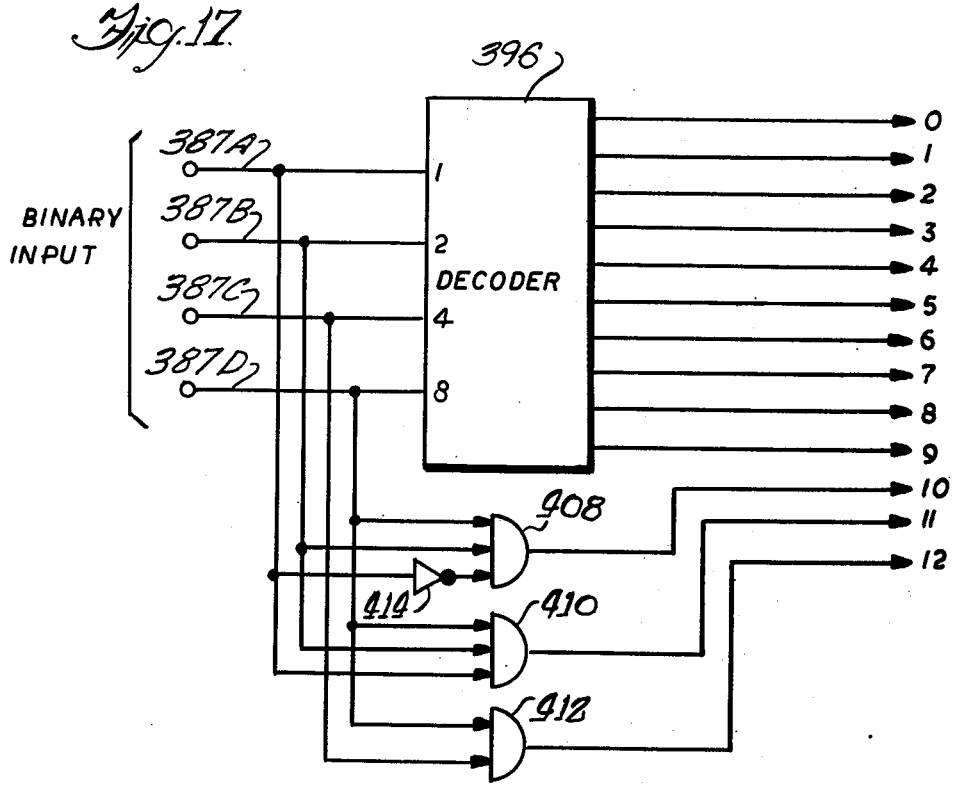
FIG. 17 is a block diagram of a decoder useful with the memory circuit of FIG. 16.

To decode the binary output from the storage registers, there is provided a different, identical binary-to-decimal data decoder for each register, one being shown in FIG. 17, having a decoder 396, four input conductors 387A, 387B, 387C and 387D, three NAND gates 408, 410 and 412 and an inverter 414. The binary-to-decimal decoder 396 provides decimal output signals corresponding to 0-9 in conventional manner in response to a five-bit binary code input and three NAND gates 408, 410 and 412 provide a decimal output signal for 10, 11 and 12.

To provide the decimal signal 10, the NAND gate 408 has one of its three inputs connected to the terminal 387D, another of its inputs connected to terminal 387B and the third of its three inputs connected through an inverter 414 to terminal 387A so that it provides an output whenever there are signals indicating 2 and 8 but not 1.

To provide a decimal 11 signal, the NAND gate 410 has a first of its three inputs connected to terminal 387D, a second of its three inputs connected to terminal 382B and a third of its three inputs connected to terminal 387A to provide an output signal when there are signals indicating 8, 2 and 1.

To provide a decimal 12 signal, the NAND gate 412 has one of its two inputs connected to terminal 387D and the other of its two inputs connected to terminal 387C to provide an output signal whenever there are signals indicating 8 and 4.

Figure 18:
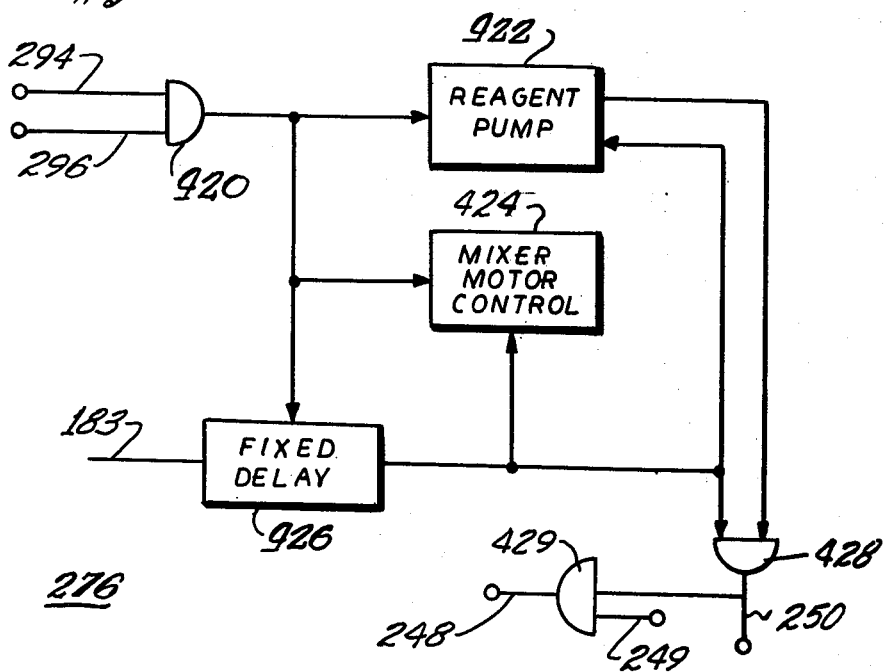
FIG. 18 is a block diagram of another variable quantity actuator shown in FIG. 13.

In FIG. 18, there is shown a block diagram of an actuator 276 for pumping a reagent, having three AND gates 428, 420 and 429, a reagent pump 422, a reagent mixer motor control 424, and a variable time delay 426.

To start a reagent pumping cycle, the AND gate 420 has one of its two inputs electrically connected to a pipette reagent command conductor 294 and the other connected to a lower pipette sensor through conductor 296, with its output being connected to the start input terminals of the reagent pump 422, the mixer motor control 424 and the time delay 426.

To control the amount of reagent deposited into a receptacle, the time delay 426 has an input connected to the command interpretor 166 (FIG. 9) through one of the conductors 183 to receive a signal setting the amount of delay, an input connected to the output of AND gate 420 to start a time delay period, with the output of the time delay being applied to the reagent pump 422, the mixer control 424 and the AND gate 428 so that the reagent and the mixer are turned on upon receiving a reagent pump command and a lowered carrier signal and turned off at the end of the time delay, with a signal being provided at the output of the AND gate 428 at the end of the delay indicating the end of the pumping time.

To provide an end-of-reagent-pumping-cycle signal, the AND gate 428 has one of its two inputs connected to the reagent pump 422 to receive a signal at the end of the pumping and the other to the output of the time delay 426, with the output of the AND gate 428 being connected to the raise/lower pipette motor control circuit 240 (FIG. 12) through a conductor 250 to cause the carrier arm 34 to be raised and connected to one of the two inputs of AND gate 429. The other input of AND gate 429 is connected to the raised pipette sensor 252, through the conductor 249, with the output of the AND gate 429 being connected to conductor 248 to indicate the end of a pipette reagent cycle.

Figure 19:
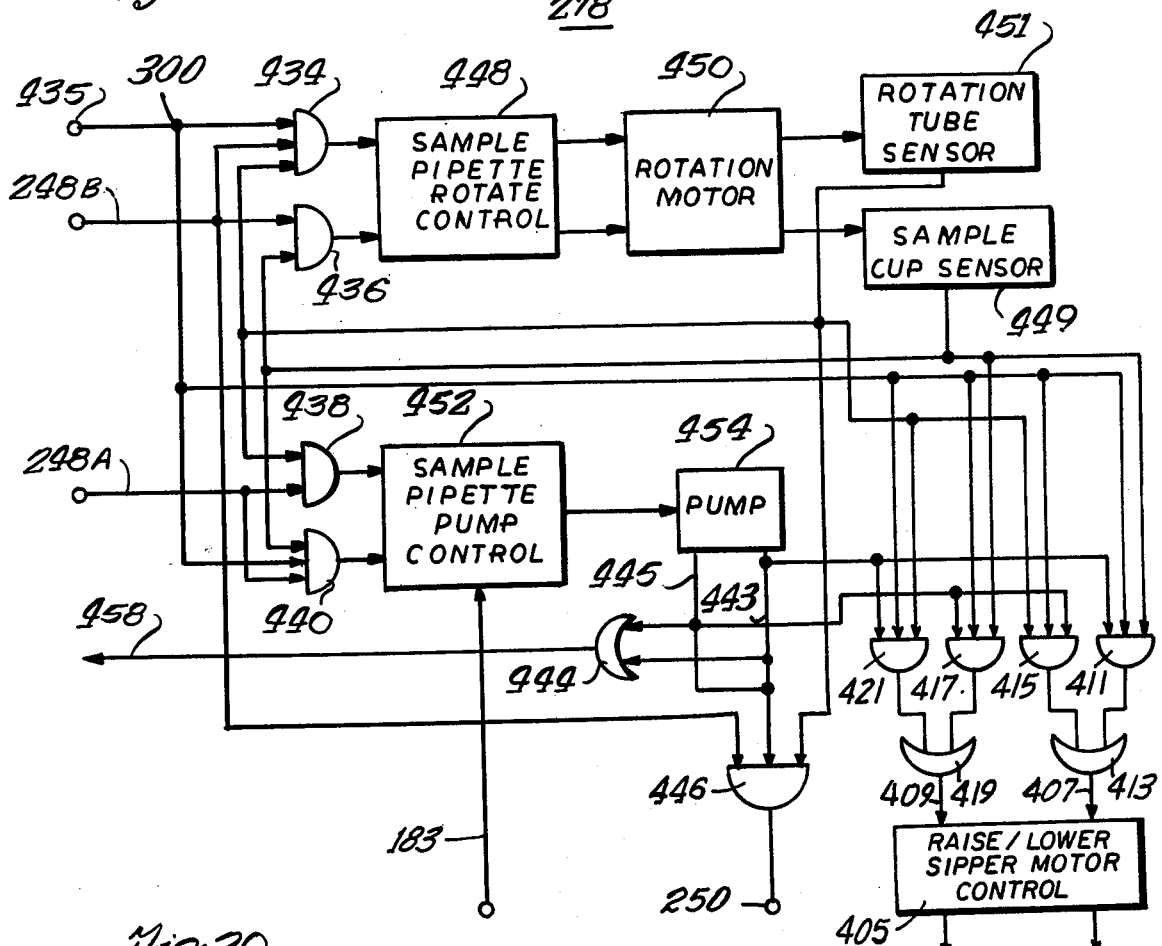
FIG. 19 is a block diagram of another variable quantity actuator shown in FIG. 13.

In FIG. 19, there is shown a block diagram of a sample pipetting system 278 for controlling the sipper mechanism 48 having five input AND gates 434, 436, 438, 440 and 446, a NOR gate 444, a sample pipette rotate control 448, a rotation motor 450 for the sample pipette, a sample pipette pump control 452, a sample pipette pump 454, a reaction tube sensor 451 and a sample cup sensor 449.

To rotate the sipper mechanism 48 (FIG. 2) to the sample cup, the AND gate 434 has a first input 248B of three inputs connected to receive a raised pipette signal from the raised pipette sensor 252 (FIG. 12), a second input connected to receive a signal from the reaction cup position sensor 449 and a third input connected to terminal 435 to receive a pipette transfer command from the command interpreter 166 (FIG. 10). Its output is connected to the sample pipette rotate control 448 which controls the rotate motor 450 to rotate the sipper mechanism 48 to the sample cup 68 (FIG. 2).

To cause the sample pump 454 to draw a sample into the pipette, the AND gate 440 has one input connected to the lowered pipette sensor 246 (FIG. 11), a second input connected to the sample cup sensor 449 and a third input connected to terminal 435, with its output being connected to the sample pipette pump control 452 to start the pump when the sample pipette is lowered into a tube and is over the sample cup.

To cause the pump 454 to expel the sample when the sample pipette is lowered into a reaction tube, the AND gate 438 has one input connected to the lowered pipette sensor 246 (FIG. 11), and the other input connected to the reaction tube sensor 451 and has its output connected to the sample pipette pump control 452 to control the pump 454. Data indicating the length of the stroke is fed into the sample pipette pump control 452 on conductor 183 to control the volume.

The pump 454 is electrically connected to OR gate 444 through a first conductor 443 through which a signal is sent indicating the end of an intake stroke and through a second conductor 445 through which a signal is sent indicating the end of a delivery stroke, with the completion of either operation by the pump resulting in a signal on conductor 458.

The AND gate 446 is opened to provide a signal on conductor 250, indicating an end of a sample transfer operation upon receiving: (1) the output signal from the pump 454 on conductor 443 indicating the end of a delivery stroke; (2) a signal on conductor 248B indicating a raised pump; and (3) a signal from the sample cup sensor 449.

To raise and lower the sipper mechanism 48 (FIG. 2), a sipper raise/lower motor 403 is connected to a raise/lower sipper motor control 405, with the raise/lower sipper motor control 405 causing the sipper raise/lower motor 403 to raise the sipper mechanism 48 in response to a signal on a first conductor 407 and to lower the sipper mechanism in response to a signal on a second conductor 409.

To raise the sipper mechanism when the syringe pump 454 is full and the sipper is at the sample cup, a first AND gate 411 has one of its three inputs connected to the sample cup sensor 449, a second of its three inputs connected to terminal 435, and a third of its three inputs connected to the output conductor 443 from the pump 454, with the output of the AND gate 411 being connected to conductor 407 through an OR gate 413.

To raise the sipper mechanism when the syringe pump 454 is empty and the sipper is at the reaction tube, a second AND gate 415 has one of its three inputs connected to the reaction tube sensor 451, a second of its three inputs connected to terminal 435 and the third of its three inputs connected to the output conductor 445 from the pump 454, with its output being connected to conductor 407 through the OR gate 413.

To lower the sipper when the syringe pump 454 is empty and the sipper is over the sample cup, a third AND gate 417 has one ot its inputs connected to the output of the sample cup sensor 449, a second of its three inputs connected to terminal 435 and the third of its three inputs connected to output conductor 445 from the pump 454, with the output of the AND gate 417 being connected to conductor 409 through the OR gate 419.

To lower the sipper when the syringe pump 454 is full and the sipper is over the reaction tube, a fourth AND gate 421 has one of its three inputs connected to the reaction tube sensor 451, a second of its three inputs connected to terminal 435 and the third of its three inputs connected to output conductor 443 of the pump 454, with the output of AND gate 421 being connected to conductor 409 through the OR gate 419.

The limits of motion of the sipper mechanism are controlled by Microswitches (not shown).

Figure 20:
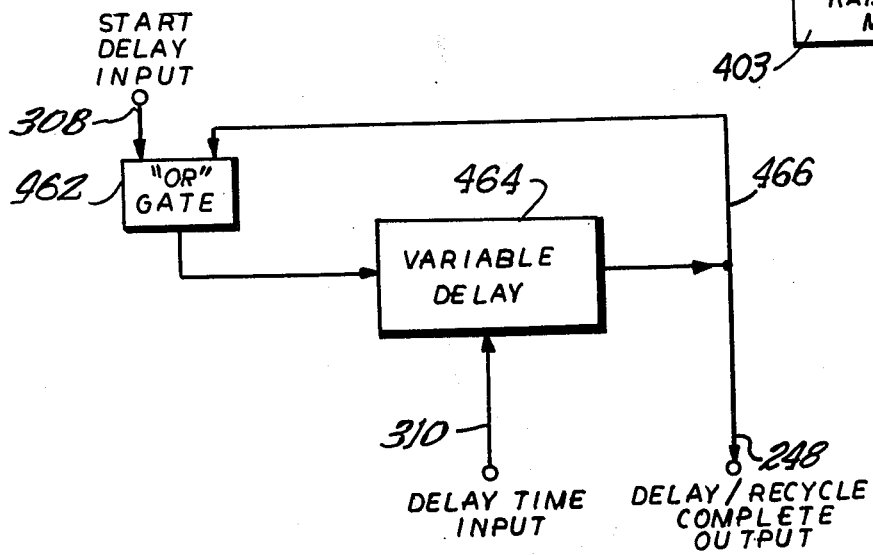
FIG. 20 is a block diagram of another variable quantity actuator shown in FIG. 13.

In FIG. 20, there is shown a delay time actuator having an OR gate 462 and a variable time delay 464. The OR gate 462 includes two inputs, one which receives a start-delay command on condutor 308 from a conductor 182 (FIG. 9) and the other which receives the output from the variable delay 464, with the output of the variable delay 464 providing the delay recycle output signal on conductor 466. The delay time data input is applied to the variable delay 464 on conductor 310 from a conductor 183 (FIG. 9) so that a recycling delay is under the control of data inserted on conductor 466.

Before operating the chemical analyzer 10, the reagents, samples, temperature and the program are prepared.

To prepare the samples, a numer of receptacle holders 64 (FIGS. 2 and 6) are chosen adequate for the analysis to be performed. These receptacle holders 64 are inserted into shuttles 22 over the support posts 66 to maintain them in place. The appropriate receptacles such as incubation tubes 72 are inserted in the receptacle holders and the shuttles with the holders are placed in the proper starting position in the outer receptacle transfer section 18, to operate with the chemical analyzer 10.

To prepare the reagent in the embodiment having shuttles within the inner receptacle tranfer section 16, receptacles 69 are placed in shuttles 22 which are within the inner receptacle transfer section and sample cups 68 are positioned over the receptacles 69 to hold the reagent. In an embodiment having a reel in the inner receptacle transfer section 16, the reel holds receptacles 69 which holds the sample cups for the reagent.

The starting materials are placed in the respective receptacles, with a starting reagent and a sample usually being contained in the sample cups of the inner receptacle tranfer section 16 and with other starting reagents being contained in the mixture or incubation tubes 72 in the outer receptacle transfer section 18.

To set the temperature of the temperature enclosure 20, the temperature sensor 140 and the motor control 142 are set to provide the proper temperature within the temperature enclosure for the reaction that is to take place.

The program to be followed is prepared on the program card (FIG. 8) by connecting together the selected ones of the busses 164 and 162 by conductive pins. This program controls the sequence of steps such as the insertion of reagents and movement of the shuttles in the chemical analyzer 10. The program card is next inserted into the program card holder 168 to establish electrical contacts between the program counter 188 and the command interpreter 166.

In operation, many different sequences of program steps are performed automatically, one after the other, depending upon the tests to be made by the chemical analyzer 10. In the preferred embodiment, eight types of commands are used. Some of the commands require a variable quantity, in which case data must be programmed into the chemical analyzer for the variable quantity and other commands represent a fixed quantity not requiring further programming. The variable quantity commands require two steps of the program card whereas the fixed step commands require only one step.

The eight types of commands which are programmable in the preferred embodiment are: (1) pipette a sample; (2) change tubes; (3) pipette a reagent; (4) time delay; (5) transfer contents of tube; (6) raise the pipette frame; (7) delay until clock recycles; and (8) go to step one.

To start a program, the push-button switch 208 (FIG. 11) in the control logic circuit 186 is depressed, electrically connecting the source of potential 216 to conductor 204 and to one of the three inputs of the AND gate 220. Since conductor 204 is connected to the inhibit line 206 (FIG. 10) of the command interpreter 166, the operation of all of the actuators is delayed while the push-button switch 208 is depressed. Because AND gate 220 has its other two inputs connected respectively to the clock pulse generator 184 and to conductor 226 through the inverter 224, a selected one of the outputs of the command interpreter 166 (FIG. 10) is connected to close the gate 220 by being connected to the conductor 226.

When the gate 220 is opened at the time the push-button switch 208 is depressed, clock pulses from the source 184 are passed through the AND gate 220 to the count input terminal of the program counter 188 causing it to step while the actuators are inhibited by the signal on conductor 204. When the program counter reaches the column of the command interpreter 166 that is connected to conductor 226, the gate 220 is closed, thus stopping the counting of the program counter 188 at that step.

When the push-button switch 208 is released, the selected command connected to conductor 226 is energized by the program counter 188 until the push-button switch 208 reaches its contacts, at which time the source 216 is connected to the one-shot multivibrator 218 causing it to apply one further pulse to the count input terminal of the program counter 188 through conductor 191 so that it steps to the next position to read the command on that position from the command interpreter 166. Since the push-button switch 208 has been released, the inhibiting pulse is no longer applied to conductor 204 so that the command of the command interpreter 166 at the starting position may be executed.

Assume that the program card (FIG. 8) is programmed by the pins 158 to perform the following sequence of eight steps: (1) pipette a sample; (2) change tubes; (3) pipette a reagent; (4) time delay; (5) transfer contents of tube; (6) raise the pipette frame; (7) delay until clock recycles; and (8) go to step one.

The first command after the push-button switch 208 is released is to pipette a sample, which is a variable data command requiring two steps.

To initiate the first step, the program counter 188 applies a signal through conductor 202A (FIG. 11) to a row 162A of the program card that is electrically connected by a program pin to column conductor 164A, which applies the signal to the command interpreter 166 (FIG. 9). The command interpreter 166 applies a pulse to the pipette sample actuator 278 (FIG. 13) through the cable 182 (FIG. 9) which is applied to terminal 435 (FIG. 19). This signal is applied to: (1) one of the three inputs of the AND gate 434, one of the other inputs coming from the reaction tube position sensor 451 and the raised pipette sensor 252, and (2) one of the three inputs to the AND gate 440; one of the other inputs coming from the sample cup position sensor 449 and the other input coming from the lowered pipette sensor 246.

Since the pipette sample actuator is a variable quantity actuator (FIG. 9) the flip-flop 211 (FIG. 11) is not reset and the next clock pulse is applied to the program counter 188 which steps to the next row of the program card. This row is a data position and thus is applied through a signal conductor 204 to the control logic circuit 186 (FIGS. 9 and 10), to inhibit the AND gates 194 from applying commands while data is read from the program card into the decoder 198 (FIGS. 10 and 17) which decodes the data and applies it through the conductors 183 to the sample pipette pump control 452 to control the volume of the sample. A signal is also applied to the control logic circuit 186 (FIG. 11) on conductor 183 through the OR gate 215 to reset the flip-flop 211, thus blocking further clock pulses from the program counter until a signal is applied through the OR gate 213 to set the flip-flop 211 at the end of the sample pipetting operation.

If the sample pipette 48 is over the reaction cup when the command to pipette a sample is given, the AND gate 434 is opened by signals on all three of its inputs while the AND gate 440 remains closed. The output from the AND gate 434 causes the rotation motor to rotate the arm 52 until the pipette is over the sample cup.

When the sample pipette 48 is over the sample cup 64, which is its normal position, and a command to pipette a sample is given, a signal from the sample cup sensor is applied to the AND gate 417 together with a signal from the pump 454 and the sample cup sensor 449 to cause the sipper mechanism to be lowered. After the sipper mechanism is lowered, the lowered pipette sensor 246 (FIG. 12), the command on conductor 300, and the signal from the sample cup sensor open AND gate 440, causing AND gate 440 to energize the sample pipette pump control 452 which causes the pump 454 to draw fluid of a volume indicated by the data stored in the sample pipette pump control 452 from the application of data on conductor 183.

When the pump 454 has drawn the programmed volume of a sample, it applies a signal through OR gate 444 to the output conductor 458 and signals are applied to the AND gate 411 from the pump 454, terminal 435 and the sample cup sensor 449 to cause the raise/lower sipper motor control 405 to energize the motor 403 to raise the sipper mechanism 48.

When the sipper mechanism is raised, a signal from raised pipette sensor 252 (FIG. 12) and from the sample cup sensor are applied to AND gate 436. These two signals open an AND gate 436 and energize the sample pipette rotate control 448. The sample pipette rotate control 448 causes the rotation motor 450 to rotate the sipper mechanism to the reaction tube 70 at which time the reaction tube sensor 451 applies a signal to the AND gates 438 and 434.

When the sipper mechanism 48 arrives at the reaction tube, signals are applied to AND gate 421 from the pump 454, the terminal 435 and the reaction tube sensor 451, to cause the sipper to be lowered into the reaction tube, at which time the lowered pipette sensor 246 (FIG. 12) and the reaction tube sensor 451 apply signals to the inputs to the AND gate 438 to energize the sample pipette pump control 452. The sample pipette pump control 452 energizes the pump 454, causing it to eject the sample into the reaction tube, after which a signal is applied through conductor 445 to: (1) the AND gate 446, which opens upon receiving this signal together with a signal from the reaction tube sensor 451 and from the command input 248B to apply a signal to conductor 250 (FIGS. 19 and 21); and (2) AND gate 417 which opens upon receiving this signal together with a signal from the reaction tube sensor 451 to energize the raise/lower sipper motor control 405 and the sipper raise/lower motor 403 to raise the sipper mechanism.

When the sipper is raised, the raised pipette sensor 252 (FIG. 12) applies a signal to AND gate 436 together with the signal from the reaction tube sensor 451, to cause the sample pipette rotate control 448 to return the sipper mechanism to a position over the sample cup for the start of another cycle.

The output from the sample cup sensor 449 cooperates with the output from the raised pipette sensor to apply a signal to conductor 248B, which conductor passes through OR gate 213 to the flip-flop 211, opening the AND gate 209 so as to cause the program counter to step one step to the next instruction.

Assume the next command is a command to change tubes.

This command originates from output conductor 202C of the program counter 188 (FIG. 11) which applies a pulse to conductor 162C of the program card (FIG. 8) causing an output on conductor 164C of the program card holder 168 (FIG. 9) to the command interpreter 166. Since the change tubes command is a fixed quantity step actuator, a signal is applied through one of the conductors 180 to the fixed quantity step actuator 172 and to the control logic circuit 186, where it causes the flip-flop 211 to be reset to stop further sequencing until the operation is completed as indicated by a signal output on conductor 249 from the fixed quantity step actuators 172.

The signal on the conductor 180 is applied to conductor 262 (FIG. 12) which in the absence of a signal on conductor 258 from the flip-flop 211 (FIG. 11) opens gate 256 to cause the tube-change motor control circuit 264 to energize the shuttle pinion motor 266 and drive the shuttle 22.

As the shuttle 22 moves into a new position, it energizes the position switch 268 which generates a pulse and applies it through the differentiator 270 to the output 248C and the tube-change motor control circuit 264, turning off the tube-change motor control circuit 264 and resetting the flip-flop 211 (FIG. 11) to indicate that the shuttle 22 has moved into position. As can be seen from FIG. 2, the motion of one of the shuttles causes all the shuttles to move in a circular path around either the outer or the inner chemical transport sections 16 or 18.

Since the flip-flop 211 has been set by the output on conductor 248B, a clock pulse is permitted to pass through gate 220 to the program counter 188, causing the next command to be initiated.

Assume that this next command is the command to pipette a reagent.

When the program counter 188 applies a pulse to the program card (FIG. 8), the program card holder 168 applies a pulse to a selected one of the conductors 164 (FIG. 9) and through this conductor to the command interpreter 166 which applies a pulse through the cable 182 to the pipette reagent actuator 276 (FIGS. 13 and 18) and to the raise/lower pipette carrier actuator 172 (FIG. 12) through a conductor 244.

Since the pipette reagent actuator 276 is a variable quantity actuator (FIG. 9), the flip-flop 211 (FIG. 11) is not reset so that a second pulse passes through the AND gate 220 to the program counter 188, causing it to step to the next position and a pulse is applied from the command interpreter 166 through the conductor 204 to the control logic circuit 186 and back to the command interpreter 166, where it inhibits the AND gates 194 (FIG. 10), with the second program step causing a readout of the program card through the decoder 198 to supply data to the pipette reagent actuator 276 (FIG. 18) through the conductor 183 which controls the stroke of the reagent pump 422.

In response to the signal on conductor 244, the carrier arm motor 238 lowers the carrier arm and thus inserts the reagent pipette into the appropriate reagent tube 70. When this has been done, the lowered pipette sensor 246 applies a signal to conductor 248A.

The pipette reagent command on the cable 182 is applied to one of the two inputs of an AND gate 420 through conductor 294 and an output signal from the lowered pipette sensor 246 (FIG. 12) is applied to the other input of the AND gate 420 through conductor 296 to cause an output signal to be applied from the AND gate 420 (FIG. 18) to the reagent pump 422, to the mixer motor control 424 and to the time delay 426, which time delay has been set by the data input on conductor 183.

The pulse to the mixer motor control 424 (FIG. 18) causes the reagent to be mixed in the tube as it is inserted. When the period of delay set into the delay 426 by the data on conductor 183 has ended, the delay 426 applies a pulse to the mixer motor control 424 and to the reagent pump 422 to stop insertion of the reagent and mixing, thus controlling the amount of reagent inserted into the reagent tube. This signal is also applied to the AND gate 428 together with a signal from the reagent pump 422, causing an output signal on a conductor 250 to be applied to OR gate 241 (FIG. 12) to raise the carrier arm 34.

The signal applied from the AND gate 428 is also applied to the AND gate 429 and cooperates with a signal on conductor 248B (FIG. 12) indicating a raised carrier arm to open the AND gate 429 and cause a signal to be applied to a conductor 248 through the OR gate 213 (FIG. 11) to set the flip-flop 211, thus permitting another clock pulse from the clock pulse generator 184 to pass through the AND gate 220 to the program counter 188.

Assume that the next command is a time delay command that establishes a delay between operations such as a delay to permit a reaction to take place in a temperature controlled zone before analysis of a sample.

To execute this command, the output of the program counter 188 (FIG. 11) is applied through the program card to a selected one of the conductors 164 and from there to the command interpreter 166 which applies an appropriate one of the output signals 182 to the conductor 308 of the variable delay actuator 280 (FIGS. 13 and 20), of the variable quantity actuators 174 (FIG. 9) and to the conductor 204 to inhibit the AND gate 194 (FIG. 10).

Since the flip-flop 211 is not inhibited by signals on conductors in the cable 182, a second pulse is applied to the program counter 188, causing it to step to another position of the program card while the AND gates 194 are inhibited, causing a data readout on cable 183 to the delay actuator 280 on conductor 310 (FIGS. 13 and 20), conductor 308 having received the previous command signal from the cable 182.

The variable delay 464 has a time period set by the data input on conductor 310 from the cable 183 and receives the command signal from conductor 308 through OR gate 462. This variable delay causes repeated signals to be applied back to the other input of the OR gate 462 and to the output conductor 466 to generate a series of pulses in a manner known in the art for the amount of delayed time set into the variable delay 464.

At the end of this period of time, a delay recycle output signal is applied to conductor 466 to initiate the recycling of a program. This signal is also applied to one of the conductors 248 to reset the flip-flop 211 and enable another clock pulse to be passed through the AND gate 209 to the program counter 188 to sequence to the next command.

Assume that the next command is to transfer the contents of a tube to a spectrophotometer.

Since this is a variable quantity command, the command output on conductor 182 is applied to conductor 287 (FIGS. 13 and 15) of the transfer fluid actuator 274 which is one of the two inputs of the AND gate 328 (FIG. 15) and to a conductor 244 (FIG. 12) of the lower pipette actuator to lower the carrier arm 34 with the pipette. When this command has been read from the program card, the program counter 189 immediately steps to the next position and the command interpreter applies a signal on conductor 204 to inhibit the AND gates 194 and to read the program card through the decoder 198 (FIG. 10) into the conductors 183. The conductors 183 are connected to conductor 348 to set a time in the variable time delay 342 and to set the variable preset counter 344 through conductor 392 (FIG. 15).

When the carrier arm has been lowered, a signal is applied to conductor 287 from conductor 248A of the lowered pipette sensor 246 (FIG. 12) which signal co-operates with the signal on conductor 285 to open the AND gate 328, activating the transfer pump control circuit 330 to start the pump 332.

As the pump draws fluid from the tube, the pump position sensor 334 senses when a given volume of fluid has been drawn and applied to the spectrophotometer. When the volume has been drawn, the pump position sensor 334 applies a signal to conductor 288 and to the time delay 336, which, after a period of time, applies a signal to one input of the AND gate 338 where it cooperates with a signal on conductor 285 from the command input to open this gate and apply a signal through conductor 340 to the variable preset counter 344 to start the printing of the results of the analysis of the spectrophotometer. The time delay provided by the time delay 336 provides sufficient time for the liquid to be scanned by the spectrophotometer.

The transfer complete signal on conductor 288, is applied to the transfer pump control circuit 330 to turn off the pump and to the conductor 250 (FIG. 12) of the raise/lower pipette carrier actuator 234 (FIG. 12) to raise the carrier 34. The signal on conductor 340 from AND gate 338 resets the variable preset counter which begins counting pulses applied to it by the variable time delay 342 at periods controlled by the data entered on conductor 348. As each pulse leaves the variable time delay 342, it is applied to the printer 352 for a readout print and to one input of the AND gate 346, the other input of the AND gate receiving a signal from the output of the variable preset counter 344 through the inverter 347 to open the gate 346 at each output pulse from the variable time delay 342.

When the end count of the preset counter 344 is reached, the output signal is inverted in the inverter 347 and closes the gate 346 to terminate the readout to the printer 352. The output from the preset counter 344 is also applied to conductor 248E to indicate the end of the readout operation, and to the flush pump control 360 through the differentiator 356 and the fixed delay 358 which energizes the flush pump control 360 a predetermined time after the final readout by the printer 352.

In response to this signal, the flush pump control 360 starts the flush pump 362 to clean the transfer conduits of fluid so as to be ready for the next reading. At the end of the flush cycle, an output signal is applied to conductor 248D by the end-of-flush sensor 364 to set the flip-flop 211 (FIG. 11) so as to pass another clock pulse from the clock pulse generator 184 to the program counter 188.

Assume the next program step is a raise pipette frame instruction.

To execute the raise-the-pipette-frame instruction, the signal from the program counter is applied through a selected one of the input conductors 162 (FIG. 8) of the program card within the program card holder and energizes a programmed one of the conductors 164 (FIG. 9) which is connected to the command interpreter 166.

The command interpreter 166 applies a signal through one of the conductors of the cable 180 (FIG. 9) to the OR gate 242 (FIG. 12) of the raise-lower pipette actuator 234 (FIG. 12) in the fixed quantity step actuators 172 (FIG. 9) to energize the raise/lower pipette motor control circuit 240. The control circuit causes the raise/lower pipette motor 238 to lift the pipette carrier 34 until the raised pipette sensor 252 indicates that the pipette is raised. At this time, the raised pipette sensor 252 applies a signal to conductor 249 which cooperates with the command signal on input 244 to open the AND gate 251, applying a signal to conductor 248B. The conductor 248B is applied to the set terminal of the flip-flop 211 through the OR gate 213 to open the AND gate 209 so as to permit an additional clock pulse to be applied to the program counter 188.

The program counter 188 steps to the next position so as to execute the next instruction, which is assumed here to go to the step one instruction programmed on the last output of the program counter. This output is not connected to the program card whatsoever, but is directly connected to the reset terminal of the program counter so as to begin execution of steps again after setting the flip-flop 211 to begin a new sequence, thus saving one position on the program card.

Any of the aforementioned program steps could have been connected to a selected one of the AND gates 194 through the OR gate 192 by not making a connection between this output and the input conductors 165 of the command interpreter 166, in which case the NOR gate 192 applies an input to the NAND gate 194F, resulting in an output on conductor 182C representing this instruction.

Obviously, more complex sequences of steps are possible. In some of these sequences, the chemical analyzer has an advantage in that it can keep a plurality of lengthy reactions in residence at one time thereby greatly increasing the thruput rate of multiple analyses. This is desirable regardless whether, in a first case, a series of identical assays on a large group of differing samples are being conducted, or in a second case, experimental parameters are being automatically varied, such as, for example, systematic variations in concentrations or amounts of two different reagents to determine the effect of this upon a group of identical samples.

A rectangular array or mathematical matrix of all possible combinations of the two different variables form a number of combinations that is the product of the two variations in the variables, such as, for example, the 120 possible combinations of ten different concentrations or amounts of a first reagent and 12 different concentrations or amounts of a second reagent from a 10 × 12 array or mathematic matrix. With a large number of different samples in the first case, or a large number of members of the array of combinations in the second case, it is desirable to have a large number of reactions proceeding it once, especially if the reaction time is long.

One way of accomplishing this can be understood from FIG. 2. A first reagent is pipetted from tube 84 into the sample cup beneath it. The sample cup is then transported stepwise leftwards to the next position. Meanwhile, a second reagent is pipetted from tube 82 into the cup beneath it, the stirrer 76 is activated, and the mixture withdrawn through tube 80 to be read by a spectrophotometer or other conventional readout device. The readout lags the time of the addition of the first reagent by the time required for five transport steps. With the transferring and stirring, or "pipetting" device (40 and 42) locations shown in FIG. 2, this arrangement allows five reactions to be kept in residence at one time. If the pipette device 40 with tubes 82 and 80 and the stirring rod 76 are moved to the left end of carrier 34, 12 reactions are kept in residence at one time. With a reaction time of 120 minutes, one determination by the readout device is made every ten minutes. This is relatively inefficient because conventional readout devices can operate much faster than this.

In another embodiment, a more advantageous operation is obtained without using reagent tube 84 and with all of the reagent being added through reagent tube 82. In this embodiment, the first reagent is pipetted repeatedly into successive sample cups through reagent tube 82 until all of the samples in the complete test run have been operated upon. Then all of the sample cups in the shuttle magazines are advanced around the remainder of receptacle transport section 18 until the first sample cup is again under tube 82. A second reagent is then introduced into the sample cup through tube 82, the stirring rod 76 activated, and the sample removed to the readout device such as a spectrophotometer by aspiration through tube 80.

To determine the effect of varying the quantities or composition of two reagents, such as in the 10 × 12 array mentioned previously, the first concentration or amount of the first reagent is pipetted into the first sample cup through tube 82, followed by the first concentration or amount of the second reagent, also pipetted through the same tube, 82. The mixture is then stirred with stirring rod 76.

The transport mechanism then advances so that the next sample cup is under tube 82. Now the same first concentration or amount of the first reagent is pipetted into the second tube, but a second concentration or amount of the second reagent is pipetted into the second tube. This continues until the last sample cup to receive the first reagent, which in the example is the 12th sample cup, is under tube 82 at which time the first concentration of the first reagent and the last concentration of the second reagent, which is the 12th concentration of the second reagent, is discharged into the sample cup. In the 13th sample cup, the second concentration or amount of the first reagent and the first concentration or amount of the second reagent is pipetted. Into the 14th tube, the second concentration of the first reagent and the second concentration of the second reagent is pipetted, into the 15th tube the second concentration or amount of the first reagent and the third concentration or amount of the second reagent is pipetted.

This process continues until each concentration of each reagent has been combined with each concentration of the other reagent. In this example, the process continues until the 120th tube into which the 10th concentration or amount of the first reagent and the 12th concentration or amount of the second reagent is pipetted. Of course, the exact sequence above need not be followed and any sequence that provides the desired combination of concentrations is workable.

The transport mechanism then advances continuously until the first sample cup is again underneath tube 82, tube 80 and stirring rod 76 at device location 40. At this time a third reagent may be added through tube 82, the mixture mixed with stirring rod 76, and aspirated to the readout device such as a spectrophotometer by withdrawal through tube 80. If all of these steps take slightly under one minute apiece, the total reaction time will be 120 minutes and the total time between the time of the first reagent addition into the first sample cup and the aspiration to the readout device of the last sample in the last sample cup will be approximately 2 hours.

This mode of operation is less than optimum if a somewhat shorter reaction time is allowable. A unique and more efficient method of operation is as follows: Consider the example of the 10 × 12 array given above. For the first 12 sample cups, the same, first amount or concentration of the first reagent is put in the first 12 cups and progressively changing (e.g. increasing) concentrations or amounts of the second reagent are placed in the sample cups, the reagents being delivered through tube 82. Operation is also similar to the preceding method for the second group of 12 sample cups, cups 13 through 24; the second concentration of the first reagent and varying concentrations of the first reagent are added.

At an appropriate reaction time, such as after the 24th sample cup, all of the sample cups are recirculated completely through the transport section 18 so that the first sample cup is again under tubes 80 and 82 and stirring rod 76. The third reagent is pipetted through tube 82, the stirring rod 76 is activated and the mixture is withdrawn to the spectrophotometer through tube 80. The 25th sample cup is then advanced so that it is beneath tube 82 and the third concentration or amount of the first reagent followed by the first concentration or amount of the second reagent is pipetted in the sample cup through tube 82. The cups are then advanced completely through the transport section so that the second cup is again under tubes 80, 82 and rod 76. The third reagent is added to the second cup, mixed, and the mixture withdrawn to the spectrophotometer through tube 80. The 26th cup is then advanced into position 40, the third concentration or amount of the first reagent and the second concentration or amount of the first reagent is added through tube 82 and then the sample cups are completely advanced through the machine so that the third sample cup is at station or position 40 where the third reagent is added, mixed and the mixture withdrawn to the spectrophotometer.

The process continues systematically in this way until all 120 cups are processed. If the reaction time required is 24 minutes, one experimental determination can be made every minute until all of the determinations in the array of 120 have been made. The total elapsed time will be 120 plus 24 equals 144 minutes.

In both methods, the reagents are applied to sample cups in succession, to initiate reactions in each cup until the desired incubation time will have elapsed after the cup having received the earliest set of reagents is positioned to remove a sample for analysis. This sample cup is then positioned and a sample removed. If more reagents or different combinations of reagents must be mixed to complete the series of arrays, the sample cups are moved and the different reagents or combination of reagents mixed in another sample cup, after which, the sample cup having the reagents in it for the longest time is moved into position and a sample removed for analysis.

One advantage of this mode of operation is that only one pipetting station or device, such as station 40, is required thereby greatly simplifying and reducing the cost of the mechanism. In addition to requiring only one station, the carrier arm 34 is not required and, more importantly, it is not necessary that the transfer passages 85 and 89 be as long as shown in FIG. 2. Instead they can be much shorter so that their scale more closely resembles that shown in the figures in U.S. Pat. No. 3,418,084. The flexible nature permits combining the functions of the sample-carrying, that would otherwise require the inner receptacle transport section 16, and reaction manipulation in the outer receptacle transport section 18. This eliminates the need for transport section 16, thereby facilitating making the transfer passages 85 and 89 shorter. The elimination of transport section 16 and the more compact nature of the overall apparatus make it much more economical to produce. An additional advantage is that the resulting smaller size requires less laboratory bench space.

The foregoing operations could be controlled by one of the prior art computer-based programmers referred to earlier such as by that described by Cembrowski, et al as well as by the programmer specifically described elsewhere in this specification.

From the above description, it can be understood that the chemical analyzer has several advantages, such as: (1) it is simple and inexpensive; (2) the shuttles may be easily removed and new ones inserted, thus permitting greater flexibility; and (3) in one embodiment, flexibility in the type of analysis being performed is enhanced by the two groups of shuttles which are movable in opposite directions.

Although a preferred embodiment has been described with some particularity, many modifications and variations in the preferred embodiment may be made without deviating from the invention. Accordingly, it is to be understood that, within the scope of the appended claims, the invention may be practiced other than as specifically described.

What is claimed is:

1. A chemical analyzer comprising:
   a plurality of movable shuttles which move through a closed path;
   a first chamber having first and second opposite ends;
   a second chamber parallel to and spaced from said first chamber and having first and second opposite ends;
   a first transfer passageway connecting said first ends of said first and second chambers;
   a second transfer passageway parallel to and spaced from said first transfer passageway and connecting said second ends of said first and second chambers;
   drive means for driving certain of said shuttles in step-by-step motion in said transfer passageways;
   said shuttles having camming means on one end for camming other shuttles in a forward direction in said chambers and connecting means on an opposite end for pulling an adjacent shuttle through a distance in said transfer passageways or from said chambers;
   a fluid transfer station;
   said shuttles being adapted to support receptacles;
   said fluid transfer station including fluid transfer means for transferring fluid from said station into said receptacle; and
   at least a portion of said closed path being of sufficient length to permit a chemical reaction to take place between two successive appearances of a given receptacle at the station.

2. A chemical analyzer according to claim 1 in which the station includes station means for analyzing the substance in one of said receptacles.

3. A chemical analyzer according to claim 1 further including a plurality of stations having means for analyzing the substance in one of said receptacles.

4. A fluid analyzer according to claim 2 in which said station includes a second fluid transfer means for transferring fluid from said station to said receptacles.

5. A fluid analyzer according to claim 1 in which a second station is provided and has provision for transferring fluid from said station to said receptacles.

6. A chemical analyzer according to claim 5 in which said first and second fluid transfer stations each include means for depositing fluid in said receptacle prior to said receptacle reaching said analyzing station.

7. A chemical analyzer according to claim 4 in which said first fluid transfer means includes a means for transferring fluid into said receptacle from said station and said second transfer includes means for withdrawing fluid from said receptacle.

8. A chemical analyzer according to claim 1 in which said station includes means to add fluid to said receptacle.

9. A chemical analyzer according to claim 1 wherein said analyzing means includes a fluid withdrawal means.

10. A chemical analyzer according to claim 9 wherein said analyzing means includes a fluid withdrawal means.

11. Apparatus according to claim 8 in which said station is positioned adjacent to one of said transfer passageways.

12. A chemical analyzer according to claim 1 comprising:
    a third transfer passageway;
    at least one shuttle in said third transfer passageway;
    drive means for driving said shuttle step-by-step at controlled times; and
    means for moving fluid between said shuttle in said third transfer passageway and a receptacle in a shuttle outside said third passageway.

13. A chemical analyzer according to claim 12 comprising:
    a third chamber having first and second ends;
    a fourth chamber spaced from and parallel to said third chamber having first and second ends;
    a fourth transfer passageway connecting said first ends of said third and fourth chambers; and
    said third transfer passageway being parallel to and spaced from said fourth transfer passageway and connecting said second ends of said third and fourth chambers.

14. A chemical analyzer according to claim 13 in which a second plurality of shuttles are located in said third and fourth transfer passageways and chambers; and
    said shuttles being driven to move in a direction opposite to the direction of motion of said first-mentioned plurality of shuttles.

15. A chemical analyzer according to claim 14 including means for synchronizing the motion of the shuttles in said first and second chambers and transfer passageways with the motion in said third and fourth transfer passageways and chambers.

16. A chemical analyzer according to claim 1 in which:
    at least one of said transfer passageways has predetermined dimensions;

said one transfer passageway being substantially enclosed except for an entrance and an exit;

said shuttles when holding said receptacles having said predetermined dimensions, whereby said shuttles and receptacles close said one transfer passageway; and temperature control means for maintaining the temperature in said one transfer passageway at at least one predetermined temperature.

17. A chemical analyzer according to claim 2 in which:

at least one of said transfer passageways has predetermined dimensions;

said one transfer passageway being substantially enclosed except for an entrance and an exit;

said shuttles when holding said receptacles having said predetermined dimensions, whereby said shuttles and receptacles close said one transfer passageway; and temperature control means for maintaining the temperature in said one transfer passageway at at least one predetermined temperature.

18. A chemical analyzer according to claim 12 in which:

at least one of said transfer passageways has predetermined dimensions;

said one transfer passageway being substantially enclosed except for an entrance and an exit;

said shuttles when holding said receptacles having said predetermined dimensions, whereby said shuttles and receptacles close said one transfer passageway; and temperature control means for maintaining the temperature in said one transfer passageway at at least one predetermined temperature.

* * * * *

UNITED STATES PATENT AND TRADEMARK OFFICE
CERTIFICATE OF CORRECTION

PATENT NO. : 4,099,921
DATED : July 11, 1978
INVENTOR(S) : Robert William Allington It is certified that error appears in the above-identified patent and that said Letters Patent are hereby corrected as shown below:

Column 3, line 56, change the words "section (shown in FIG. 2) 16" to "section 16 (shown in FIG. 2)".
Column 4, line 48, before the words "section 16", insert the words "To transfer a chemical from inner receptacle".
Column 5, line 15, change the word "rotation" to "rotating".
Column 9, line 59, change "181" to "191".
Column 12, line 15, change "FIG. 99" to "FIG. 9".
Column 16, line 35, change "ANd gate" to "AND gate".
Column 18, line 59, change "384-384D" to "384A-384D".
Column 22, line 9, change the word "tranfer" to "transfer".
Column 22, line 19, change the word "tranfer" to "transfer".
Column 23, line 42, change the comma to a semicolon.
Column 24, line 47, change "21" within the parenthesis to "12".
Column 25, line 9, change "249" to "248".
Column 25, line 29, change "248B" to "248C".
Column 28, line 6, change the words "raise-lower" to "raise/lower".
Column 28, line 55, change the word "from" to "form".

Signed and Sealed this

Twenty-fifth Day of December 1979

[SEAL]

Attest:

SIDNEY A. DIAMOND

Attesting Officer  Commissioner of Patents and Trademarks